(12) United States Patent
Henschke et al.

(10) Patent No.: US 8,742,143 B2
(45) Date of Patent: *Jun. 3, 2014

(54) PROCESS FOR THE PREPARATION OF PROSTAGLANDIN ANALOGUES

(71) Applicant: ScinoPharm Taiwan, Ltd., Tainan (TW)

(72) Inventors: Julian P. Henschke, Tainan (TW); Yuanlian Liu, Suzhou (CN); Yung-Fa Chen, Tainan (TW); Dechao Meng, Suzhou (CN); Ting Sun, Kunshan (CN)

(73) Assignee: Scinopharm Taiwan, Ltd., Tainan (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/851,848

(22) Filed: Mar. 27, 2013

(65) Prior Publication Data
US 2013/0211128 A1 Aug. 15, 2013

Related U.S. Application Data

(62) Division of application No. 12/905,439, filed on Oct. 15, 2010, now Pat. No. 8,436,194, which is a division of application No. 12/421,185, filed on Apr. 9, 2009, now Pat. No. 7,897,795.

(60) Provisional application No. 61/123,527, filed on Apr. 9, 2008.

(51) Int. Cl.
C07D 307/02 (2006.01)
C07C 69/76 (2006.01)
C07C 69/74 (2006.01)

(52) U.S. Cl.
USPC .............................. 549/501; 560/55; 560/121

(58) Field of Classification Search
USPC ..................... 549/501; 560/55, 121
See application file for complete search history.

(56) References Cited

U.S. PATENT DOCUMENTS

| | | | |
|---|---|---|---|
| 5,106,750 A | 4/1992 | Wong et al. | |
| 5,618,959 A | 4/1997 | Trampota et al. | |
| 6,214,611 B1 | 4/2001 | Fox et al. | |
| 6,313,341 B1 | 11/2001 | Murata et al. | |
| 6,852,880 B2 | 2/2005 | Ham et al. | |
| 7,109,371 B2 | 9/2006 | Clissold et al. | |
| 7,897,795 B2 * | 3/2011 | Henschke et al. | 549/501 |

FOREIGN PATENT DOCUMENTS

| | | |
|---|---|---|
| GB | 1384024 | 2/1975 |
| JP | 56-46833 | 4/1981 |
| JP | 63-77837 | 4/1988 |
| JP | 3077878 | 4/1991 |
| JP | 5213924 | 8/1993 |
| JP | 9020788 A | 1/1997 |
| WO | WO95/33845 | 12/1995 |
| WO | WO2005/058812 A2 | 6/2005 |

OTHER PUBLICATIONS

Dygos, J. H. et al., "An efficient synthesis of the antisecretory prostaglandin enisoprost", Journal of Organic Chemistry, vol. 56, 1991, pp. 2549-2552.

Linderman et al., Synthesis of and Analysis of Thiol Additions to β-Alkylα-a, β-unsaturated Trifluoromethyl Ketones, J. Org. Chem. 1994,59, 957-962.

Renaldo et al., Palladium-Catalyzed Coupling of Acid Chlorides with Organotin Reagents: Ethyl (E)-4-(4-Nitrophenyl)-4-oxo-2-butenoate[2-Butenoic acid, 4-(4-Nitrophenyl)-4-oxo-, ethyl ester, (E)-], Organic Syntheses, Coll. vol. 8, p. 268 (1993); vol. 67, p. 86 (1989).

Marshall et al., Generation of Noracemic 2-(t-Butyldimethylsilyloxy)-3-Butynyllithium From (S)-Ethyl Lactate:[(S)-4-(t-Butyldimethylsilyloxy)-2-Pentyn-1-OL], Organic Syntheses, vol. 81, p. 157 (2005).

Rodriguez et al., An Efficient Asymmetric Synthesis of Prostaglandin E1 , Eur. J. Org. Chem. 1999, 2655-2662.

Hodgson et al., A Two-directional Synthesis of the C58-C71 fragament of Palytoxin, Org. Biomol. Chem., 2004, 2, 373-386.

Fox et al., An Entantiocovergent Syntheis of (R)-4-Aryloxy-1-butyne-3-ols for prostanoid Side Chains, Adv. Synth. Catal. 2002, 344, No. 1, 50-56.

Floyd, Prostagalandins and Congeners. 18. Synthesis of Cyclopentenolon Precursors to Prostaglandsins from 2,5-Dihydro-2,5-dimethoxyfurans, J. Org. Chem. vol. 43, No. 9, 1978, 1641-1643.

* cited by examiner

Primary Examiner — Nizal Chandrakumar
(74) Attorney, Agent, or Firm — Enshan Hong; Kent H. Cheng; VLP Law Group LLP

(57) ABSTRACT

A process for preparing a prostaglandin analogue comprising a step of converting a compound of formula (8'):

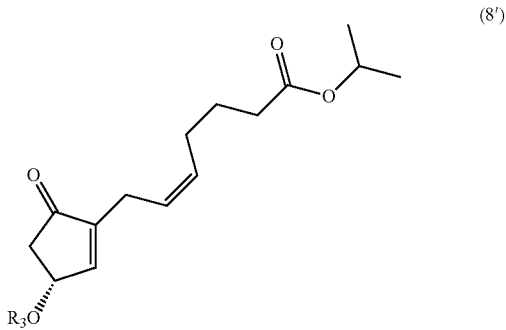

to the prostaglandin analogue, wherein $R_3$ represents hydrogen or a hydroxyl protecting group.

8 Claims, No Drawings

PROCESS FOR THE PREPARATION OF PROSTAGLANDIN ANALOGUES

RELATED APPLICATIONS

This application is a divisional of U.S. patent application Ser. No. 12/905,439 which was filed with the U.S. Patent and Trademark Office on Oct. 15, 2010, which is a divisional of U.S. patent application Ser. No. 12/421,185 which was filed with the U.S. Patent and Trademark Office on Apr. 9, 2009, which claims priority from U.S. Provisional Patent Application Ser. No. 61/123,527 which was filed on Apr. 9, 2008. The entire content of these related applications is explicitly incorporated herein as reference.

BACKGROUND OF THE INVENTION

1. Field of the Invention

The present application is directed to intermediates for preparing prostaglandin analogues and processes for preparing prostaglandin analogues and intermediates thereof.

2. Description of the Related Art

Natural prostaglandins have a unique structure based on prostanoic acid and exhibit a broad range of physiological activities even when present in extremely small amounts, attracting interest of many organic synthetic chemists. Therefore, various processes to synthesize structural analogues of natural prostaglandins have been developed and disclosed for both academic interest and also for manufacturing purposes.

However, there is still need for a more simple, practical, and/or economical process for producing prostaglandin analogues.

SUMMARY OF THE INVENTION

The first aspect of the present application is a process for preparing a prostaglandin analogue of formula (11)

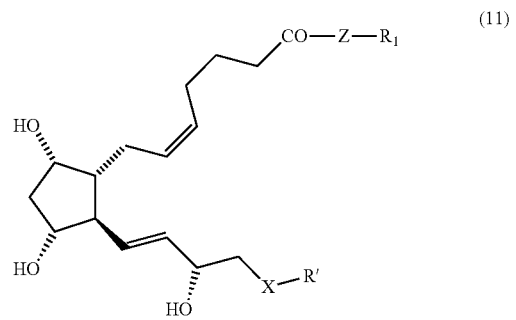

wherein
$R_1$ represents H, $C_1$-$C_5$-alkyl, or benzyl;
X represents $CH_2$, O, or S;
Z represents O or NH; and
R' represents $C_2$-$C_4$-alkyl; phenyl optionally substituted by halogen, $C_1$-$C_5$-alkyl, $C_1$-$C_4$-alkoxy, $CF_3$, $C_2$-$C_4$-polyhaloalkyl, or $C_1$-$C_3$-aliphatic acylamino; 5- or 6-membered heterocycle containing one or more hetero atoms selected from a group consisting of nitrogen, oxygen and sulfur; $C_3$-$C_7$-cycloalkyl; or $C_3$-$C_7$-cycloalkenyl.

The process comprises steps of:
(a) converting a compound of formula (4):

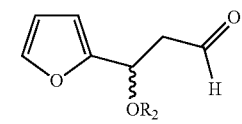

to a compound of formula (5):

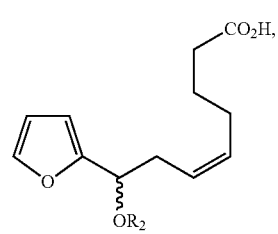

wherein $R_2$ represents a hydroxy-protecting group;
(b) esterifying and deprotecting the compound of formula (5) to give a compound of formula (6):

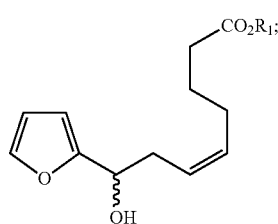

(c) converting the compound of formula (6) to a compound of formula (8):

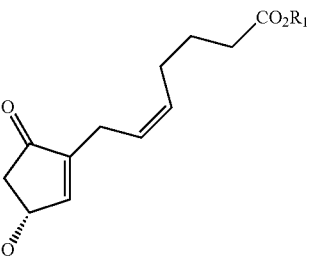

wherein $R_3$ represents a hydroxy-protecting group;
(d) reacting the compound of formula (8) with a compound of formula (9):

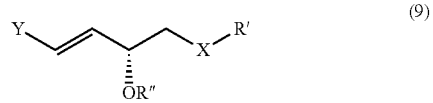

to give a compound of formula (10):

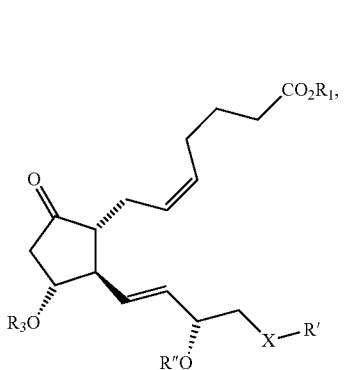

(10)

wherein Y represents a metal complex, R" represents a hydroxy-protecting group; and (e) converting the compound of formula (10) to give the compound of formula (11).

The second aspect of the present application provides a process for preparing a cyclopentenone having the formula (8) as provided, wherein $R_1$ represents H, $C_1$-$C_5$-alkyl, or benzyl; $R_3$ represents H or a hydroxy-protecting group. The process comprises the steps (a)-(c) as stated above. Preferably, $R_1$ is isopropyl.

Preferably, the metal complex described above is a copper (I) salt. More preferably, the metal complex is a copper(I) salt selected from the group consisting of a lithium cuprate, a lithium cyanocuprate, a dilithium methylcyanocuprate, a dilithium 2-thienylcyanocuprate, a lithium vinylcuprate, a dilithium vinylcyanocuprate and combinations thereof.

In accordance with a preferred embodiment of the present invention, the hydroxy-protecting group used in the present invention is selected from the group consisting of triethylsilyl (TES), triisopropylsilyl (TIPS), dimethylphenylsilyl, diphenylmethylsilyl, tert-butyldiphenylsilyl (TBDPS), tert-butyldimethylsilyl (TBS), tetrahydropyranyl (THP), triphenylmethyl and combinations thereof. More preferably, the hydroxy-protecting group is tert-butyldimethylsilyl (TBS).

The third aspect of the present application provides a compound of formula (6) as described above. Specifically, a compound of formula (6)

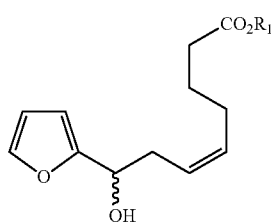

(6)

wherein $R_1$ represents H, $C_1$-$C_5$-alkyl, or benzyl. Preferably, $R_1$ is isopropyl.

The fourth aspect of the present application provides a process for preparing a prostaglandin analogue of formula (11) as defined above. The process comprise a step of converting a compound of formula (8'):

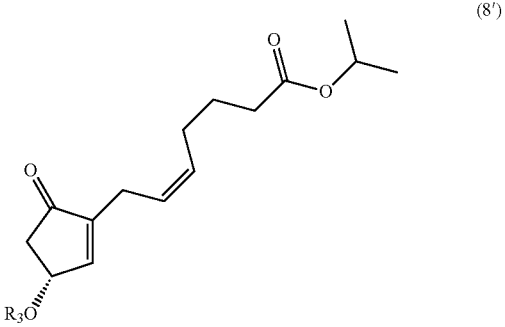

(8')

to the compound of formula (11), wherein $R_3$ represents hydrogen or a hydroxyl protecting group. Preferably, the compound of formula (11) is travoprost or bimatoprost.

As shown above, in accordance with at least one embodiment of the present invention (e.g., the first to third aspects of the present application as described above), to make the compound of formula (6), the intended side chain is not coupled with a furfural directly. Rather, Wittig reaction and esterification are carried out to obtain the furan intermediate (6) from the compound (4). More cis-enriched compound (6) can be obtained in such a process.

In addition, in accordance with at least one aspect of the present invention (e.g., the third and fourth aspects of the present application), similar prostaglandins or prostaglandin derivatives (e.g., travoprost or bimatoprost) can be obtained rapidly and efficiently by using the same diverging intermediate (e.g., compound of 8'). The diverging route is economical on a manufacturing scale when making a plurality of prostaglandins or prostaglandin derivatives.

The advantages of applying the isopropyl ester intermediates of formula 8' to make travoprost and bimatoprost include:

(a) The isopropyl group acts as both a protecting group (for the carboxyl group during the synthesis of bimatoprost) and part of the product itself (for travoprost).

(b) The isopropyl group is superior to the methyl group and tert-butyl group. The problem with the methyl and tert-butyl groups, when attached to carboxylate functions, is that the methyl and tert-butyl groups are acid and aqueous acid sensitive and can be partially or completely cleaved during the rearrangement step (6→7A or 7B, see the scheme provided below). This problem with the methyl group is reported in *J. Org. Chem.* 1991, 56, 2549-2552 for the synthesis of the prostaglandin enisoprost—in this report, the authors had to re-attach the methyl group after the rearrangement step, leading to one extra synthetic step in the reaction sequence.

(c) The isopropyl group is treated specifically as a protecting group when used in the synthesis of bimatoprost. The synthesis of bimatoprost using the diverging route is simply an extension from the synthesis of travoprost.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

The following scheme is provided as an embodiment to illustrate, but not to limit the present invention.

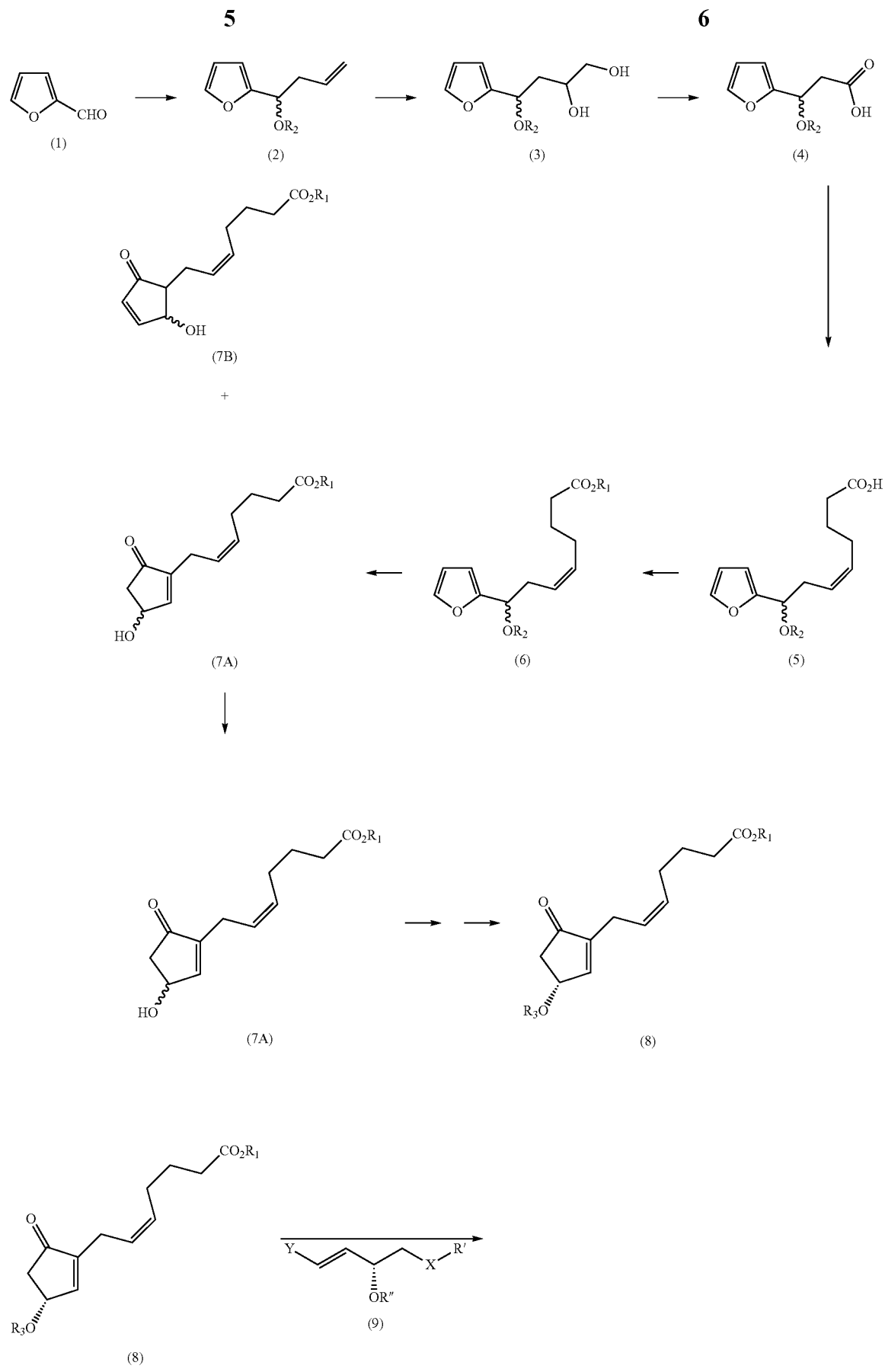

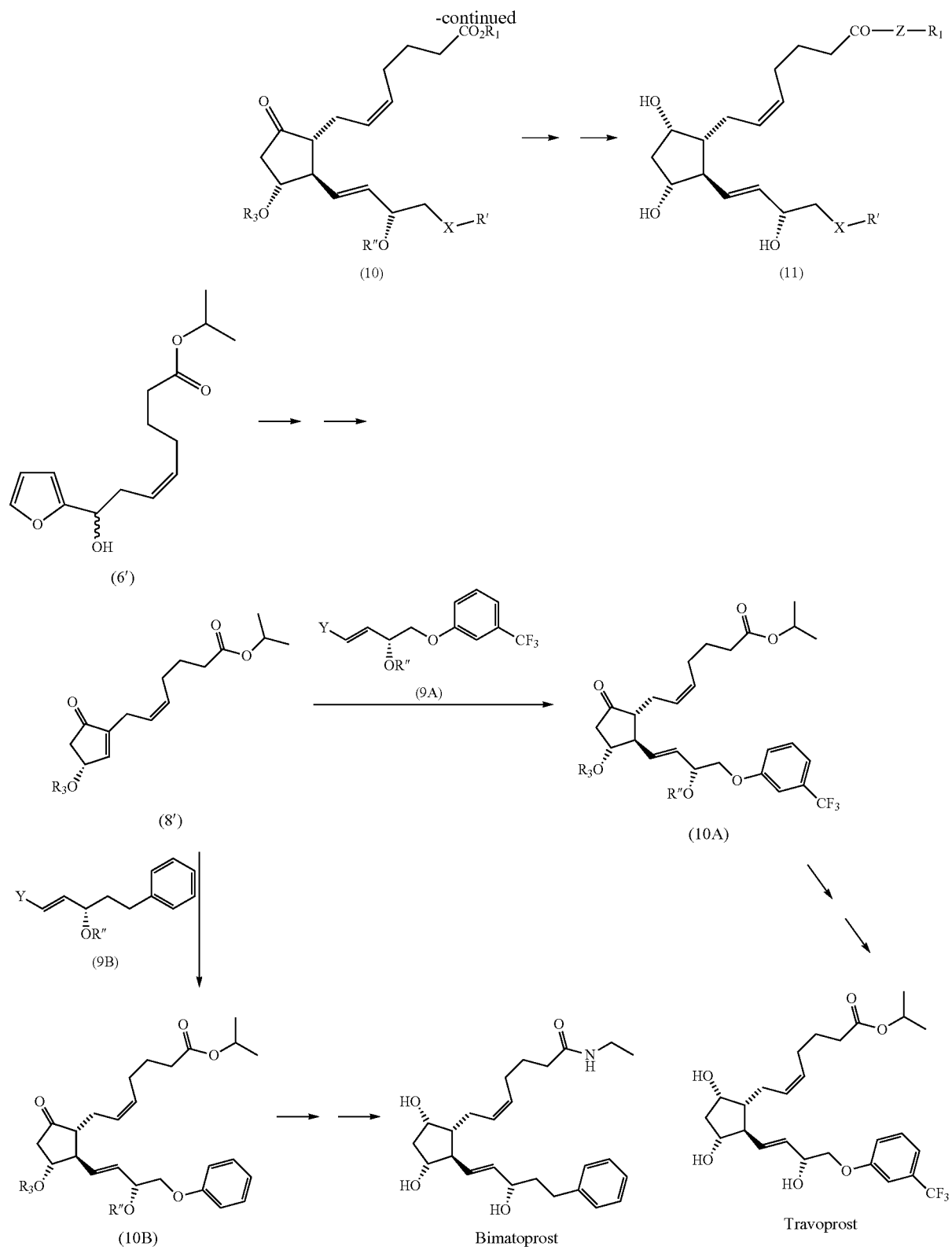

As shown above, the starting material is furfural (1). A furfural sequentially reacts with an allyl metal reagent, a protecting reagent, a hydroxylating reagent, and a cleavage reagent to give a compound (4). Then, the aldehyde group of the compound (4) reacts with an ylide to give compound (5). Next, the compound (5) is esterified and deprotected to give compound (6), which is rearranged to give a mixture of hydroxy-cyclopentenone compounds of (7A) and (7B). The compound (7B) is then converted to the compound (7A). The resulted racemic compound (7A) is resolved and purified to give optically active (R)-form. After that, the optically active (R) form of compound (7A) reacts with a protecting reagent to give the diverging intermediate (8). Finally, the diverging intermediate (8) can be converted into a prostaglandin analogue.

As an embodiment, the diverging intermediate (8) may react with a cuprate compound (9) to give a compound (10). The compound (10) may then be modified optionally and deprotected to give a prostaglandin analogue (11).

As an embodiment, the aldehyde group of compound (4) may react with $Ph_3PCH(CH_2)_3COONa$ to give compound (5), which may then be esterified and deprotected to give compound (6'), which can subsequently be converted to compound (8') after several reaction steps. Afterwards, the isopropyl ester intermediate (8') may respectively react with cuprate compound (9A) or (9B) to give compound (10A) or (10B), which may then be modified and deprotected to give travoprost or bimatoprost.

As a preferred embodiment, the compound of formula (1) may be first 1) reacted with an allyl halide in the presence of zinc, magnesium, alkyl lithium or samarium(II) iodide, in particular zinc, and then 2) the resulting compound of step 1) may be protected to give the compound of formula (2) wherein $R_2$ represents a hydroxy-protecting group.

Preferably, the process of the present invention may comprise (1) reacting a compound of formula (I): $X[Ph_3P(CH_2)_4COOH]$ (I), wherein X represents a halide, with a metal containing base in a solvent system to give a compound of formula (II): $Ph_3PCH(CH_2)_3COOM$ (II), wherein M represents a metal ion, and (2) reacting the compound of formula (4) with the compound of formula (II) at a low temperature of from −100 to 0° C. to give the compound of formula (5). More preferably, the low temperature is −80 to −15° C., in particular −30 to −70° C.

The examples of the metal containing base used in the present invention include bases containing sodium, potassium and lithium individually or in combination, in particular sodium containing base. For example, the metal containing base may be selected from the group consisting of NaHMDS, KHMDS, t-BuOK, n-BuLi, LiHMDS, and combinations thereof. More preferably, the metal containing base is NaHMDS. When the lithium containing base, e.g., n-BuLi, is used, the solvent system preferably contains HMPA, TTPA or DMSO.

Preferably, the solvent system used in the reaction of converting the compound of formula (I) to the compound of formula (II) is THF or 2-methyl-THF. And the reaction between the compound of formula (4) and the compound of formula (II) is conducted at the low temperature of from −80 to −15° C., in particular from −70 to −50° C.

As another preferred embodiment, the solvent system used in the reaction of converting compound (I) to compound (II) is THF mixed with a co-solvent. And the reaction between the compound (4) and compound (II) is conducted at the low temperature of from −50 to −30° C. The co-solvent is preferably selected from the group consisting of TTPA, HMPA, DMSO, and combinations thereof. More preferably, the co-solvent is TTPA.

Preferably, the amount of the co-solvent is 5-25% v/v, in particular 5-10%, of the solvent system.

In accordance with a preferred embodiment of the present invention, the process of the present invention comprises steps of:
(1) deprotecting the compound of formula (5),
(2) forming a salt of the de-protected compound of formula (5),
(3) purifying the salt of step (2) to remove the trans-isomer and obtain the cis-isomer enriched salt, and
(4) esterifying the cis-isomer enriched salt to give the compound of formula (6).

The salt of the de-protected compound of formula (5) is preferably a benzylamine salt.

The racemic compound of formula (7A) is preferably resolved at a temperature of 30-50° C., more preferably 38-42° C., most preferably about 40° C. Applicants surprisingly found that compared to conventionally used room temperature, a higher temperature can result in a higher conversion rate and a much faster process.

As a preferred embodiment, the compound of formula (11) is travoprost. The process may comprise steps of:
(a) reacting a compound of formula (8'), wherein $R_3$ represents a hydroxy-protecting group, with a compound of formula (9A), wherein Y represents a metal complex, R" represents a hydroxy-protecting group, to give a compound of formula (10A); and
(b) converting the compound of formula (10A) to give travoprost.

The hydroxy-protecting group is preferably tert-butyldimethylsilyl (TBS).

The metal complex is preferably a copper(I) salt, more preferably, a copper(I) salt selected from the group consisting of dilithium methylcyanocuprate, a dilithium 2-thienylcyanocuprate, and combinations thereof.

As another preferred embodiment, the compound of formula (11) may be bimatoprost, $R_3$ in the formula 8' represents a hydroxy-protecting group. The process may comprise a) reacting the compound of formula (8') with a compound of formula (9B):

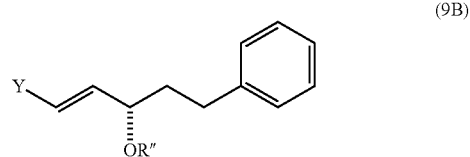

wherein
Y represents a metal complex,
R" represents a hydroxy-protecting group,
to give a compound of formula (10B):

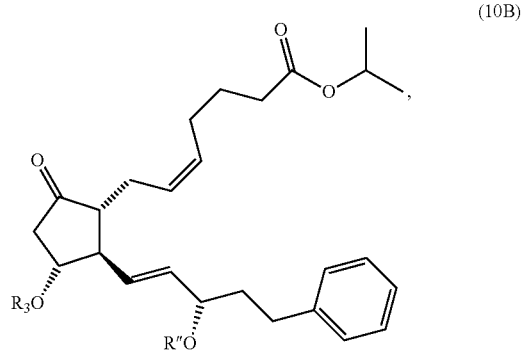

and
(b) converting the compound of formula (10B) to bimatoprost.

Preferably, the hydroxy-protecting group is tert-butyldimethylsilyl (TBS). The metal complex is preferably a copper(I) salt, more preferably, a dilithium methylcyanocuprate or a dilithium 2-thienylcyanocuprate.

The step (b) of converting the compound of formula (10B) to bimatoprost may comprise steps of:

(1) reducing the ketone group of compound of formula (10B);
(2) deprotecting the reduced form of the compound of formula (10B); and
(3) reacting the resultant compound of step (2) with ethylamine to give the bimatoprost.

Alternatively, steps (2) and (3) can be conducted in the reverse order.

Preferably, the above step (3) of converting the resultant compound of step (2) to bimatopros is conducted in the presence of 40 to 80% v/v ethylamine in methanol, more preferably, 70% v/v ethylamine in methanol. The amination must be conducted in the absence of any water; otherwise hydrolysis to the carboxylic acid will occur.

As an embodiment, the compound of formula (9) is purified before converting into its metal complex by (1) resolving a racemic mixture of the compound of formula (9'):

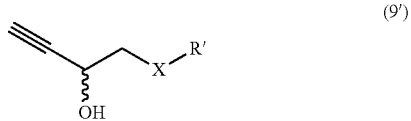

(9')

to give the corresponding acetate with desired configuration and the corresponding alcohol with undesired configuration, (2) converting the alcohol with undesired configuration in the reaction mixture of step (1) directly to give the corresponding formate with desired configuration, and
(3) converting the acetate and formate with desired configuration in the reaction mixture of step (2) directly to give the compound of formula (9') with desired configuration.

In accordance with a preferred embodiment of the present invention, the process of making the compound of formula (9A) comprises:

(a) providing a compound (A3):

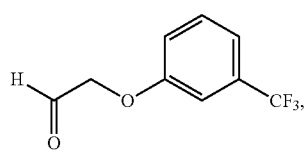

(A3)

(b) reacting the compound (A3) with a with a magnesium halide acetylide or a lithium, sodium or potassium acetylide to give a racemic mixture of compound (A4):

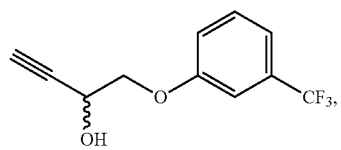

(A4)

(c) purifying the racemic mixture of compound (A4) to give the (R)-form of compound (A4), and
(d) converting the (R)-form of compound (A4) to the compound (9A).

Preferably, the above step (c) of purifying the racemic mixture of compound (A4) comprises steps of:

(1) resolving a racemic mixture of formula (A4) to give (R)-form compound (A4) acetate and (S)-form compound (A4) alcohol,
(2) converting (S)-form compound (A4) alcohol in the reaction mixture of step (1) directly to give (R)-form compound (A4) formate, and
(3) converting (R)-form compound (A4) acetate and formate in the reaction mixture of step (2) directly to give (R)-form of compound (A4).

In accordance with another preferred embodiment of the present invention, the process of making the compound of formula (9B) comprises steps of:

(a) reacting 3-phenyl-1-propanal with a magnesium halide acetylide or a lithium, sodium or potassium acetylide to give a racemic mixture of compound (B1):

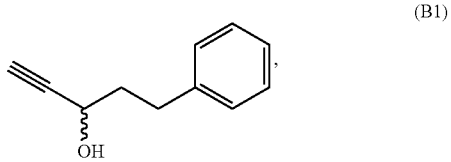

(B1)

(b) purifying the racemic mixture of compound (B1) to give the (S)-form of compound (B1), and
(c) converting the (S)-form of compound (B1) to the compound (9B).

Preferably, the above step (b) of purifying the racemic mixture of compound (B1) comprises steps of:

(1) resolving a racemic mixture of formula (B1) to give (S)-form compound (B1) acetate and (R)-form compound (B1) alcohol,
(2) converting (R)-form compound (B1) alcohol in the reaction mixture of step (1) directly to give (S)-form compound (B1) formate, and
(3) converting (S)-form compound (B1) acetate and formate in the reaction mixture of step (2) directly to give (S)-form of compound (B1).

EXAMPLES

The following examples are provided to illustrate, but not to limit, the present invention.

The abbreviations used in the following examples are first explained below:

| | |
|---|---|
| TTPA | Tris(N,N-tetramethylene)phosphoric acid triamide |
| TBSCl | tert-Butyldimethylsilyl chloride |

-continued

| | |
|---|---|
| THF | Tetrahydrofuran |
| (DHQ)₂PHAL | Hydroquinine 1,4-phthalazinediyl diether (4-[(R)-[(5S,7R)-5-ethyl-1-azabicyclo[2.2.2]octan-7-yl]-(6-methoxyquinolin-4-yl)methoxy]-1-[(R)-[(5R,7R)-5-ethyl-1-azabicyclo[2.2.2]octan-7-yl]-(6-methoxyquinolin-4-yl)methoxy]phthalazine) |
| NMO | N-Methylmorpholine-N-oxide |
| LHMDS | Lithium Hexamethyldisilazide (LiN(SiMe3)2) |
| NaHMDS | Sodium Hexamethyldisilazide (NaN(SiMe3)2) |
| KHMDS | Potassium Hexamethyldisilazide (KN(SiMe3)2) |
| NMP | N-methyl-2-pyrrolidone |
| DMPU | 1,3-Dimethyl-3,4,5,6-tetrahydro-2(1H)-pyrimidinone |
| DCC | Dicyclohexylcarbodiimide |
| DMAP | 4-dimethylaminopyridine |
| DBU | 1,8-Diazabicyclo[5.4.0]undec-7-ene |
| TBAF | Tetra-n-butylammonium fluoride |
| DEAD | Diethyl azodicarboxylate |
| AIBN | Azobis(isobutyronitrile |

Part I: Preparation of the Diverging Intermediate, Steps A to J

Step A: Allyl Addition and Protection—Synthesis of 1-(tert-butyldimethylsilyloxy)-1-(furan-2-yl)-but-3-ene (2b)

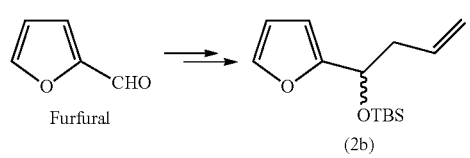 [SMILES: O=Cc1ccco1 ; C=CCC(O[Si](C)(C)C(C)(C)C)c1ccco1]

Example 1

Two-Pot Synthesis of the Compounds (2b)

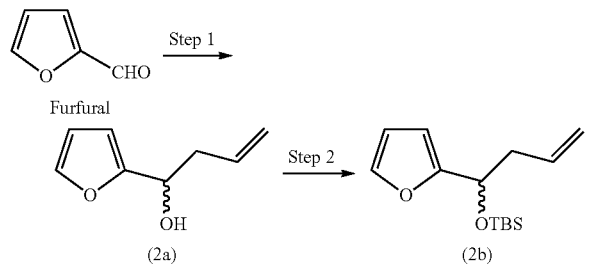

(Barbier reaction) To a mixture of zinc (about 75 g) and anhydrous THF (about 100 mL) at 60-65° C. was added a 4% mixture of allyl bromide (about 140 g) and furfural (about 100 g) in anhydrous THF (about 100 mL). The mixture was stirred at 60-65° C., and then the remaining former mixture was added. After the addition was complete, the mixture was heated to 60~70° C. Methyl tert-butyl ether (MTBE) (about 250 mL) was added and the reaction mixture was cooled to about −5° C. and then 2N HCl (about 500 mL) was added. The mixture was extracted twice with MTBE (about 250 mL each). The combined organic layers was washed twice with saturated aqueous NaCl (about 200 mL), dried (MgSO₄), filtered and concentrated under reduced pressure to give 157 g of crude compounds (2a) (89% GC purity) in 97% yield.

Alternatively, the compounds (2a) can be obtained by reacting furfural with allyl Grignard reagents, e.g. allyl magnesium bromide.

(TBS-protection) To a cold solution of crude compounds (2a) (about 150 g) and imidazole (about 100 g) in DMF (about 400 mL) was added TBSCl (about 150 g) dissolved in DMF (about 200 mL). After the addition was complete the mixture was heated to 20~30° C. Water (about 400 mL) and n-heptane (about 500 mL) were added and the reaction mixture was extracted twice with n-heptane (about 250 mL each). The combined organic layers was washed with saturated aqueous NaCl (about 300 mL) and concentrated under reduced pressure to give 280 g of the crude compounds (2b). This was purified by distillation under reduced pressure and the fraction was collected giving about 150 g (57% yield) of 97% GC pure compounds (2b).

Alternatively, the compounds (2b) can be obtained by one-pot synthesis of using Barbier reaction and in situ TBS-protection.

Step B: Synthesis of 4-(tert-butyldimethylsilyloxy)-4-(furan-2-yl)-butane-1,2-diol (3a)

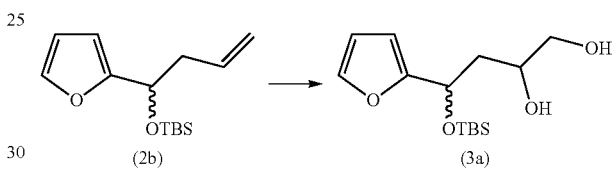

Example 2

A mixture of the compounds (2b) (about 20 Kg), K₂OsO₂(OH)₄ (about 0.1 Kg) and hydroquinine 1,4-phthalazinediyl diether ((DHQ)₂PHAL) (about 0.2 Kg) in acetone (about 86 Kg) was stirred at room temperature for a short period of time and then cooled to 10-15° C. A solution of N-methylmorpholine-N-oxide (NMO) (about 11 Kg) in water (about 36 Kg) was added and the temperature remained within 10-25° C. The reaction was stirred at room temperature. Na₂SO₃ (about 16 Kg) in water (about 47 Kg) was added to quench the reaction, and the mixture was then heated to 40-43° C. for 1.5 h, filtered and the filter cake was washed with acetone (about 27 Kg). The combined filtrate was concentrated under reduced pressure. The concentrated residue was extracted twice with ethyl acetate (EtOAc) (about 33 Kg each) and the combined organic layer was washed with saturated aqueous NaCl (about 41 Kg), and then concentrated under reduced pressure providing about 20 Kg of 90% GC pure crude compounds (3a).

Alternatively, the step of synthesizing the compounds (3a) can be conducted in aqueous t-BuOH.

Step C: Synthesis of 3-(tert-butyldimethylsilyloxy)-3-(furan-2-yl)-propanal (4a)

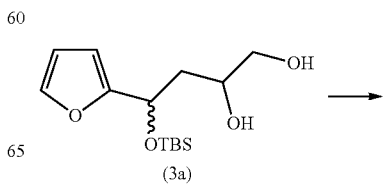

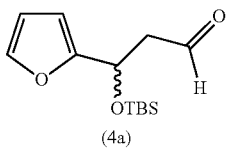

(4a)

Example 3

One-Step Synthesis

To a stirred solution of NaIO$_4$ (about 20 Kg) in water (about 62 Kg) under argon was added solution of compounds (3a) (about 20 Kg) in acetone (about 58 Kg). The resulting mixture was stirred. The reaction mixture was filtered and the filter cake was washed with MTBE (about 15 Kg). The combined filtrate was separated and the aqueous layer was extracted with MTBE (about 15 Kg), the combined organic layer was washed with saturated aqueous NaCl (about 27 Kg) and then dried over anhydrous MgSO$_4$ for 2 h under argon. The mixture was filtered through silica gel and the filter cake was washed with MTBE (about 50 Kg). The filtrate was concentrated under reduced pressure to furnish compounds (4a) (about 18 Kg) as a brown oil which was used directly without purification in the next step.

Alternatively, the compounds (4a) can be obtained by One-pot synthesis of using the reaction disclosed in EXAMPLE 2 and in situ the reaction disclosed in EXAMPLE 3.

Step D: Wittig Reaction—Synthesis and purification of (Z)-8-(tert-butyldimethylsilyloxy)-8-(furan-2-yl)-oct-5-enoic acid (5a)

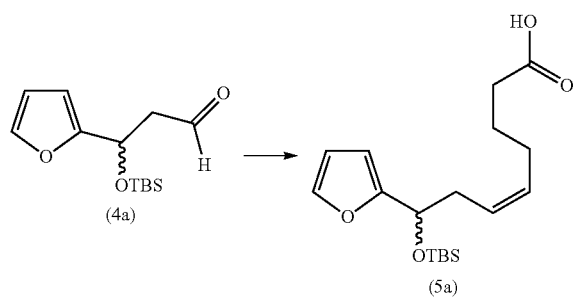 [SMILES: CC(C)(C)[Si](C)(C)OC(CC=O)c1ccco1 ; CC(C)(C)[Si](C)(C)OC(C/C=C\CCCC(=O)O)c1ccco1]

Example 4

No Co-Solvent at −70 to −60° C.

To a cold suspension of (4-carboxybutyl)triphenylphosphonium bromide (BrPPh$_3$(CH$_2$)$_4$COOH) (about 40 Kg) in THF (about 190 Kg) under argon was added a solution of sodium hexamethyldisilazide (NaHMDS) (2 M solution in THF, about 80 Kg). The resulting dark orange mixture was stirred for 0.5 h and then cooled to −70~−60° C. A pre-cooled solution of compounds (4a) (about 18 Kg) in THF (about 50 Kg) was then added. The mixture was stirred at −70~−60° C. Acetone (about 6 Kg) was added at this temperature, stirred, and followed by EtOAc (about 150 Kg) and then saturated aqueous NH$_4$Cl (about 298 Kg). After the addition was complete the reaction temperature was warmed to about −5° C. and the aqueous layer was separated. Some water (about 55 Kg) was added to the aqueous layer to dissolve the precipitated solid and was then extracted with EtOAc (about 50 Kg) and the combined organic layers was washed twice with saturated aqueous NaCl (about 73 Kg each) and then concentrated under reduced pressure to provide the crude compounds (5a).

After this crude compounds (5a) were esterified (see EXAMPLE 5) to give isopropyl (Z)-8-(tert-butyldimethylsilyloxy)-8-(furan-2-yl)-oct-5-enoate (5b), they were then deprotected (see EXAMPLE 6) to give isopropyl (Z)-8-(furan-2-yl)-8-hydroxy-oct-5-enoate (6a) that HPLC analysis indicated that it contained 90.6% of the desired cis-isomer and 9.4% of undesired trans-isomer.

Alternatively, THF in this Wittig reaction can be replaced by 2-methyl-THF. NaHMDS can be replaced by KHMDS, t-BuOK, n-BuLi, or LiHMDS.

Furthermore, this Wittig reaction was also conducted under the following alternative conditions. The yields (over three steps from the compounds 3a) and the GC purities of the resulting compounds (5b) by following Example 5, and the isomer ratios of the resulting compounds (6a) by following Example 6 are also listed.

| Reagent | Solvent | Reaction temperature | Base | Yield and GC purity of (5b) | Isomer ratio of (6a) (cis- to trans-) |
|---|---|---|---|---|---|
| (4-carboxybutyl)triphenylphosphonium bromide | 4.5% TTPA in THF | −15° C. | NaHMDS | 75%; 92% | 90.0:10.0 |
| (4-carboxybutyl)triphenylphosphonium bromide | 9% TTPA in THF | −15° C. | NaHMDS | 71%; 88% | 91.1:8.9 |
| (4-carboxybutyl)triphenylphosphonium bromide | 19% TTPA in THF | −15° C. | NaHMDS | 72.2; 85% | 91.2:8.8 |
| (4-carboxybutyl)triphenylphosphonium bromide | 24% TTPA in THF | −15° C. | NaHMDS | 75%; 64.4% | 92.2:7.8 |
| (4-carboxybutyl)triphenylphosphonium bromide | 9% TTPA in THF | −35° C. | NaHMDS | 81%; 96.1% | 91.8:8.2 |
| (4-carboxybutyl)triphenylphosphonium bromide | 9% TTPA in THF | −55° C. | NaHMDS | 61%; 88% | 91.4:8.6 |

-continued

| Reagent | Solvent | Reaction temperature | Base | Yield and GC purity of (5b) | Isomer ratio of (6a) (cis- to trans-) |
|---|---|---|---|---|---|
| (4-carboxybutyl)triphenylphosphonium bromide | 5% TTPA in THF | −55° C. | NaHMDS | 46%; 83% | 91.1:8.9 |
| (4-carboxybutyl)triphenylphosphonium bromide | 9% TTPA in THF | −78° C. | NaHMDS | 52%; 96% | 91.5:8.5 |
| (4-carboxybutyl)triphenylphosphonium bromide | 10% HMPA in THF | −15° C. | NaHMDS | 43%; 81% | 90.9:9.1 |
| (4-carboxybutyl)triphenylphosphonium bromide | 10% HMPA in THF | −15° C. | LiHMDS | 74%; 96% | 90.5:9.5 |
| (4-carboxybutyl)triphenylphosphonium bromide | 10% DMSO in THF | −15° C. | NaHMDS | 43%; 61% | 91.3:8.7 |

TTPA represents tris(N,N-tetramethylene)phosphoric acid triamide
LHMDS represents lithium hexamethyldisilazide (LiN(SiMe3)2)
KHMDS represents potassium hexamethyldisilazide (KN(SiMe3)2)
HMPA represents hexamethylphosphoramide
NMP represents N-methyl-2-pyrrolidone
DMPU represents 1,3-dimethyl-3,4,5,6-tetrahydro-2(1H)-pyrimidinone
t-BuOK represents potassium t-butoxide Step E: Esterification—Synthesis of Isopropyl (Z)-8-(tert-butyldimethylsilyloxy)-8-(furan-2-yl)-oct-5-enoate (5b)

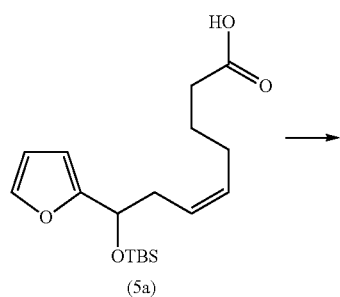

(5a)

heated under reflux. After 4 hours more $K_2CO_3$ (about 14 g) and 2-iodopropane (about 18 Kg) was added. Water (about 112 Kg) and MTBE (about 83 Kg) was added and the mixture was stirred for 20 min. The aqueous layer was separated and was extracted with MTBE (about 26 Kg), the combined organic layer was washed twice with saturated aqueous NaCl (about 47 Kg each) and then concentrated under reduced pressure to furnish a brown oil. The oil was dissolved in EtOAc (about 20 Kg) and n-heptane (about 46 Kg) was added causing a solid to precipitate. The solid was filtered and washed with 1:3 EtOAc/n-heptane (about 34 Kg) and the filtrate was concentrated under reduced pressure to provide oil. The oil was purified by column chromatography and then concentrated under reduced pressure to provide 94% GC pure compounds (5b), 17 Kg, 60% yield over three steps from the compounds (3a).

Alternatively, other bases, such as $Cs_2CO_3$ or 1,8-diazabicyclo[5.4.0]undec-7-ene (DBU), can be applied in this Esterification reaction.

Alternatively, this esterification reaction can be conducted by using dicyclohexylcarbodiimide (DCC), 4-dimethylaminopyridine (DMAP) and isopropanol.

Step F: Synthesis of isopropyl (Z)-8-(furan-2-yl)-8-hydroxy-oct-5-enoate (6a)

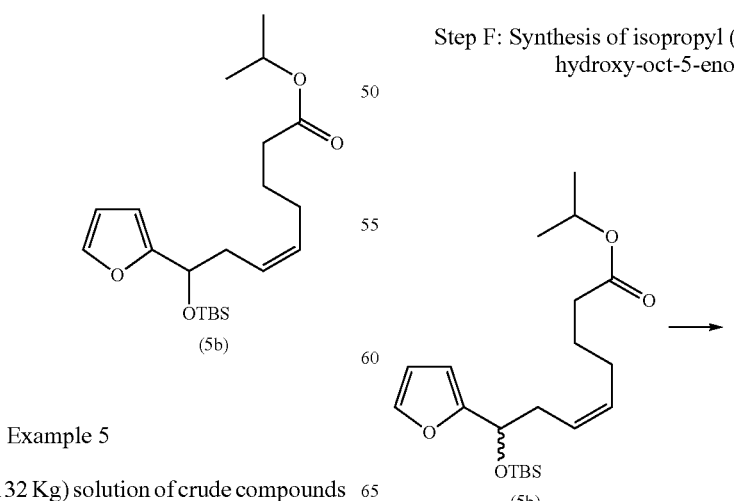

Example 5

To an acetone (about 132 Kg) solution of crude compounds (5a) prepared in EXAMPLE 4 was added $K_2CO_3$ (about 28 Kg) and 2-iodopropane (about 35 Kg) and the mixture was

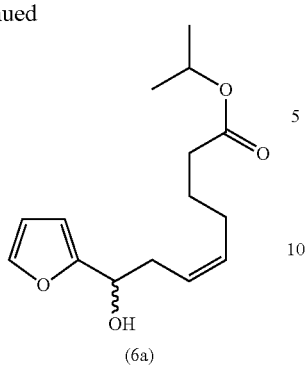

Example 6

Deprotection

A mixture of the compounds (5b) (about 16 Kg) prepared in EXAMPLE 5 and tetra-n-butylammonium fluoride trihydrate (TBAF.3H$_2$O) (about 13 kg) in THF (about 70 Kg) was stirred at 35~45° C. Saturated aqueous NH$_4$Cl (about 23 Kg) and NaCl (about 0.16 Kg) was added. The aqueous layer was separated and extracted with EtOAc (about 110 Kg) and then the combined organic layer was concentrated under reduced pressure. EtOAc (about 110 Kg) was added, stirred for several minutes, and then the resulting solution was washed twice with water (about 46 Kg each). The organic layer was concentrated under reduced pressure to give crude compounds 6a as brown oil. This was used directly in the next step without purification. HPLC analysis indicated that it contained 90.6% of the desired cis-isomer and 9.4% of undesired trans-isomer.

Example 7

Three Step Synthesis of Cis-Isomer Enriched Compounds (6a)

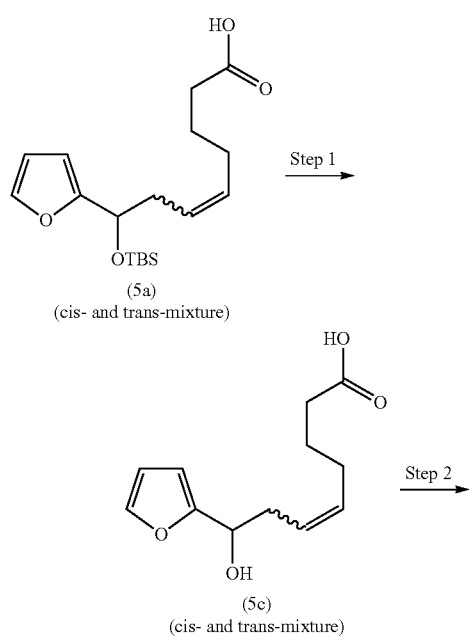

Step 1 Deprotection

A mixture of the compounds 5a (about 35 g) and TBAF.3H$_2$O (about 40.6 g) in THF (about 175 mL) was stirred at 35~45° C. Saturated aq. NH$_4$Cl (about 140 mL) and EtOAc (about 140 mL) were added and the mixture was stirred vigorously for 30 min. The layers were separated and the organic layer was concentrated in vacuo. EtOAc (about 140 mL) was added, stirred for several minutes, and then the resulting solution was washed twice with water (about 140 mL each). The organic layer was concentrated in vacuo to give about 20 g crude compounds (5c) as brown oil. The oil was then purified by column chromatography and then concentrated to provide 95% GC pure compounds (5c) (about 13 g, 60% yield). HPLC analysis showed that it contained 90.8% of the desired cis-isomer and 9.2% of the undesired trans-isomer.

Step 2 Salt Formation and Recrystallization

To a mixture of the above prepared compounds (5c) (about 5 g) and MTBE (about 13 mL) was added benzylamine (about 2.4 g). The mixture formed two layers. The mixture was stirred at about 0° C. until the sticky oily lower layer produced a solid. The solid was filtered, washed with anhydrous MTBE (about 5 mL) and was dried under vacuum giving 4.7 g (ca. 64% yield) of crude compounds (5c) benzylamine salt ((5c).BnNH$_2$). HPLC analysis showed that it contained 90.8% of the desired cis-isomer and 8.5% of the undesired trans-isomer. The crude compounds (5c) benzylamine salt (about 3 g) was mixed with EtOAc (about 4.5 mL), stirred at 35~45° C. for 15~30 minutes and then cooled to 15~25° C. for 3 hours. The resulting solid was filtered, washed with three times with EtOAc (about 3 mL each) and dried under vacuum. HPLC analysis showed that the compounds (5c) benzylamine salt (about 1.6 g, 52% yield) was enriched in the cis-isomer (96.4% cis-isomer) and contained only 3.6% of the undesired trans-isomer. By contrast HPLC analysis of the crystallization mother liquors contained 18% of the undesired trans-isomer and 82% of the cis-isomer.

Step 3 Esterification

To an acetone (about 10 mL) solution of the cis-isomer enriched compounds (5c) benzylamine salt (about 1 g) was added $K_2CO_3$ (about 4 g) and 2-iodopropane (about 5 g). The mixture was heated under reflux. Water (about 15 mL) and MTBE (about 15 mL) were added and the mixture was stirred for 20 min. The layers were separated and the aqueous layer was extracted with MTBE (about 5 mL) and the combined organic layers were washed twice with saturated aq. NaCl (about 5 mL each) and concentrated in vacuo to furnish about 0.9 g (66% yield) of the compounds (6a) as a brown colored oil. HPLC analysis showed that the compounds (6a) was enriched in the cis-isomer (98.1% cis-isomer) and contained only 1.9% of the undesired trans-isomer.

Step G: Rearrangement—Synthesis of isopropyl (Z)-7-(3-hydroxy-5-oxo-cyclopent-1-enyl)-hept-5-enoate (7a') and isopropyl (Z)-7-(2-hydroxy-5-oxo-cyclopent-3-enyl)-hept-5-enoate (7b')

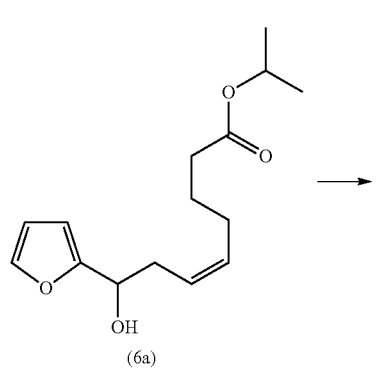

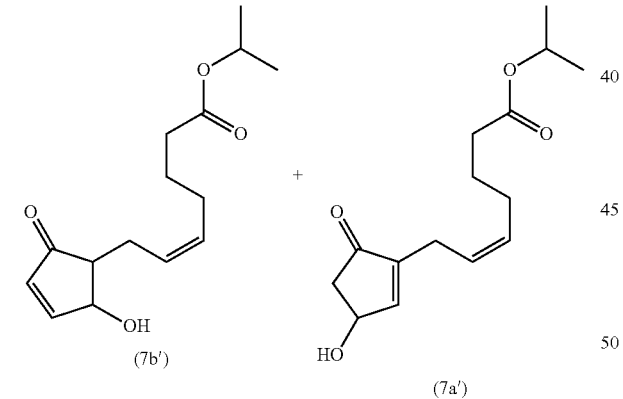

Example 8

To a mixture of $ZnCl_2$ (about 65 Kg) and water (about 73 Kg) was added crude compounds (6a) prepared in EXAMPLE 6 or 7, dioxane (about 86 Kg) and hydroquinone (about 4.6 g). The mixture was heated in a $N_2$ atmosphere under reflux. The product mixture was cooled and then the dioxane was evaporated under reduced pressure. EtOAc (about 75 Kg) and saturated aqueous $NH_4Cl$ (about 44 Kg) were added into the reaction mixture. The aqueous layer was separated and extracted with EtOAc (about 36 Kg) and then the combined organic layer was washed with saturated aqueous NaCl (about 44 Kg) and concentrated under reduced pressure to give the mixture of compounds (7a') and (7b'), in racemic forms.

Step H: Isomerisation—Synthesis of the Racemic Compounds (7a')

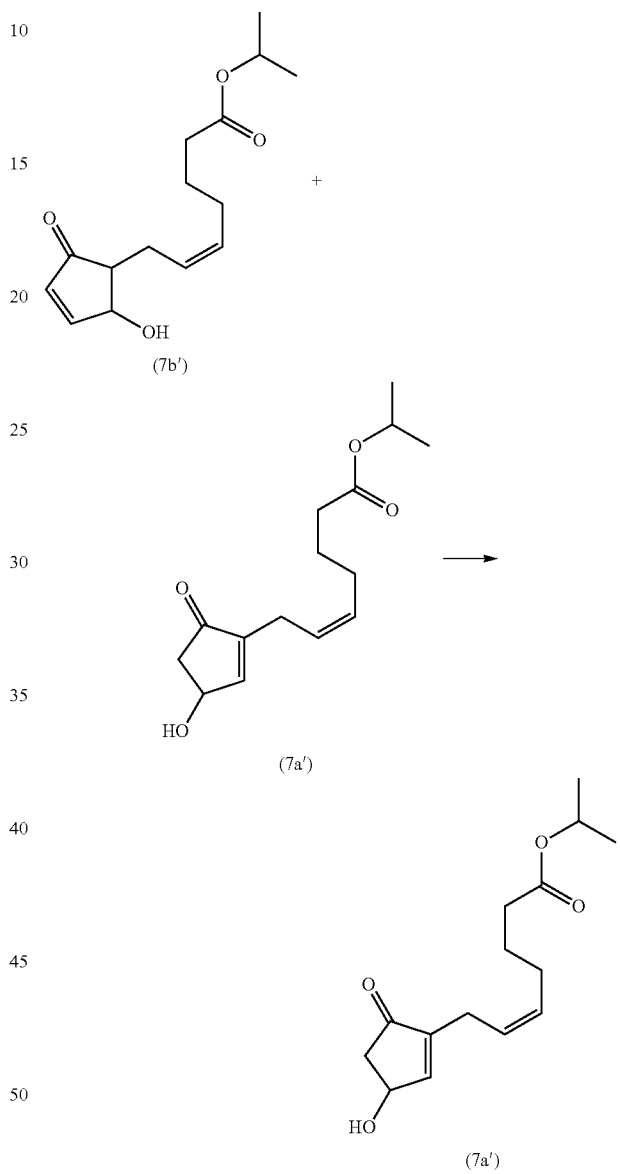

Example 9

Toluene (about 81 Kg), $Et_3N$ (about 5.5 Kg) and chloral (about 1.3 Kg) were then added to the mixture of compounds (7a') and (7b') prepared in EXAMPLE 8 and the solution was stirred for 12 h. More triethylamine ($Et_3N$) (about 2.7 Kg) and chloral (about 0.4 Kg) were added and the reaction was stirred for a further 3 h. Saturated aqueous $NH_4Cl$ (about 44 Kg) was added. The aqueous layer was separated, filtered and then extracted with toluene (about 29 Kg), the combined organic layer was washed with saturated aqueous NaCl (about 23 Kg) and concentrated under reduced pressure to give a brown oil (about 10 Kg). The oil was purified by column chromatography to furnish 100% GC pure compounds (7a') in racemic form (about 4.4 Kg).

Step I: Enzymatic Resolution and
Purification-Synthesis of the (R) Form of
Compounds (8b)

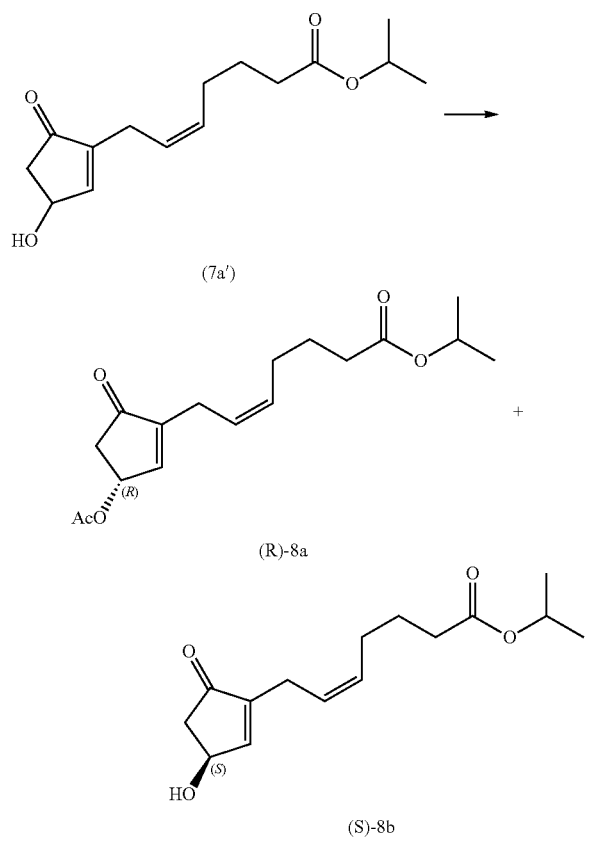

| Enzyme w/w of (7a') | Solvent | Reaction temperature | Yield; Enantiomeric purity |
|---|---|---|---|
| 100% w/w Porcine Pancreas Lipase Type II | n-heptane/ vinyl acetate = 6.25:1 | 38-42° C. | Purified (R-8a): 31%; 94% e.e. (S-8b): 59%; 42% e.e. |
| 50% w/w Lipase PS "Amano" SD | vinyl acetate | 30° C. | Crude mixture of (R-8a) (95.7% e.e., 59.1% HPLC purity) and (S-8b) (89.4% e.e., 37.7% HPLC purity) |
| 25% w/w Lipase PS "Amano" IM | vinyl acetate | 40° C. | Crude mixture of (R-8a) (94.6% e.e., 58.2% HPLC purity) and (S-8b) (100% e.e., 40.2% HPLC purity) |
| 5% w/w Lipase PS "Amano" IM | MTBE/vinyl acetate = 3.6:1 | 50° C. | Crude mixture of (R-8a) (97.4% e.e., 54.2% HPLC purity) and (S-8b) (87.6% e.e., 42.3% HPLC purity) |

The mixture containing the undesired enantiomer, (S)-form compounds (8b), or the isolated (S)-form compounds (8b) could be further recycled by Mitsunobu reaction as in EXAMPLE 11 and cleavage of the thus formed formate compound (compounds 8c) to provide the (R)-form of compounds (8b) that could be enantiomerically enriched by a second enzymatic resolution cycle.

Example 11

The Mitsunobu Reaction of (S)-Form Compounds
(8b) (in a Mixture) to (R)-Form Compounds (8c)

Example 10

The First Resolution by Using 50% w/w Lipase PS
"Amano" in Vinyl Acetate at 40° C.

To the solution of racemic compounds (7a') (about 4.6 Kg) prepared in EXAMPLE 9 and vinyl acetate (about 35 Kg) was added Lipase PS "Amano" (about 2.4 Kg, approximately 50% w/w of compounds 7a'). The mixture was stirred at 38-42° C. The reaction mixture was then filtered through a layer of celite and the filter cake was washed three times with EtOAc (about 4 Kg each) and then concentrated to give yellow-brown oil composing a mixture of (R)-form compounds (8a), an acetate compound, (96.7% e.e.) and (S)-form compounds (8b), an alcohol compound, (89.6% e.e.). The mixture was used directly in the Mitsunobu reaction, EXAMPLE 11.

Furthermore, the first enzymatic resolution was also conducted under the following alternative conditions, and some of the resulting mixtures of (R)-form compounds (8a) and (S)-form (8b) were separated by column chromatography. The yields and the enantiomeric purities of the crude/purified compounds (R)-form (8a) and (S)-form (8b) are also listed.

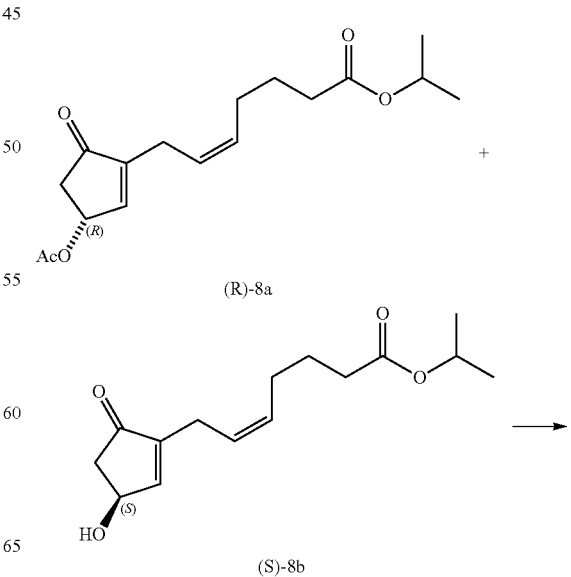

-continued

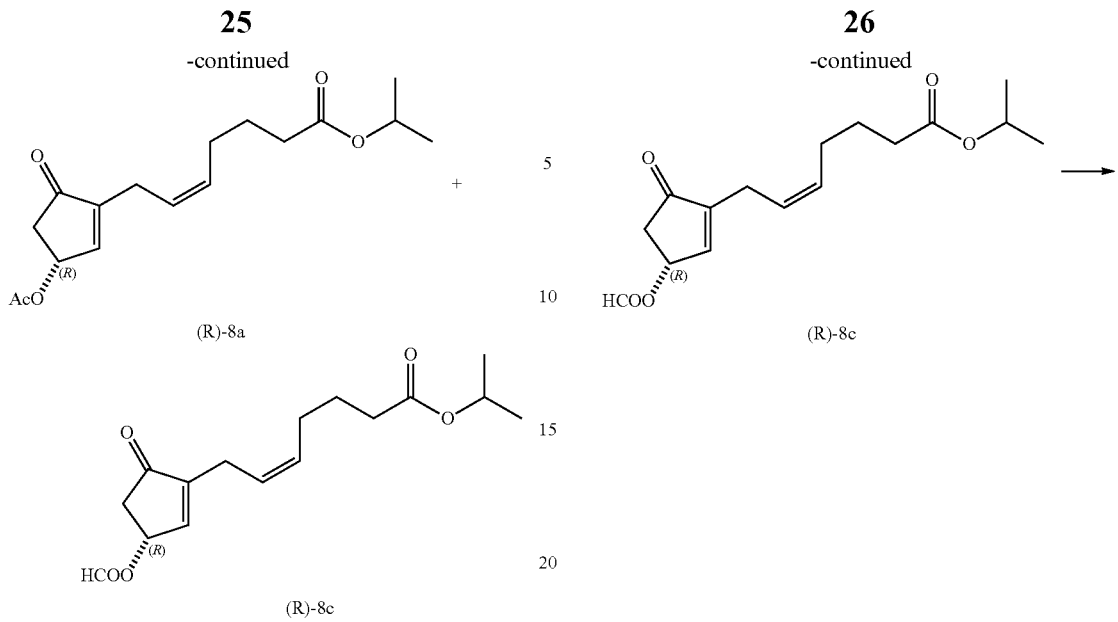

(R)-8a (R)-8c

To a cold mixture of (R)-form compounds (8a) and (S)-form (8b) prepared in EXAMPLE 10, triphenylphosphine (Ph₃P) (about 7 Kg) and formic acid (about 1 Kg) in THF (about 22 Kg) was added a solution of diethyl azodicarboxylate (DEAD) (about 4.7 Kg) in THF (about 4.5 Kg) whilst maintaining a temperature of 0-10° C. After the addition was complete the cooling bath was removed and the reaction mixture was warmed to 20-25° C. and was stirring. The reaction mixture was concentrated under reduced pressure, EtOAc (about 5.6 Kg) was added into the hot residue followed by n-heptane (about 13 Kg) causing precipitation of a white solid. The suspension was cooled, filtered and the filter cake was washed three times with 1:5 EtOAc/n-heptane (about 3 Kg each), concentrated and purified by column chromatography providing a mixture (about 5 Kg) mixture of (R)-form compounds (8a) and (R)-form (8c), a formate compound, that was used directly in the next step as in EXAMPLE 12.

This Mitsunobu reaction also could be applied on the isolated (S)-form compounds (8b), so only the (R)-form compounds (8c) will be formed under this situation.

Example 12

Guanidinolysis of a Mixture of (R)-Form Compounds (8a) and (8c) to the (R)-Form of Compounds (8b)

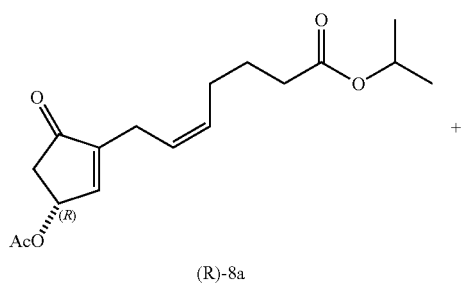

(R)-8a

+

(R)-8c

→

(R)-8b

To a chilled methanol (MeOH) (about 20 Kg) solution of a mixture (about 5 Kg) of (R)-form compounds (8a) and (8c) prepared in EXAMPLE 11 was added solution of guanidine in MeOH (0.5 M, about 14 Kg). Acetic acid (AcOH) (about 0.5 g) was added and the mixture was stirred for 15 min before the mixture was warmed to room temperature. The product mixture was concentrated under reduced pressure to remove MeOH. EtOAc (about 22 Kg) and water (about 48 Kg) were added and the separated aqueous layer was extracted with EtOAc (about 22 Kg). The combined organic layer was washed with water (about 24 Kg) followed by saturated aqueous NaCl (about 24 Kg) and then dried over MgSO₄ for 2 h. The solution was filtered and the filter cake was washed three times with EtOAc (about 5 Kg each) and concentrated to give crude 91% e.e. (R)-form of compounds (8b) (about 4.5 Kg, 94% GC pure). This (R)-form enriched compound (8b) could be further enantiomerically purified by using a second enzymatic resolution.

This guanidinolysis reaction also could be applied on the (R)-form compounds (8c) isolated from the mixture prepared in EXAMPLE 11, or the (R)-form compounds (8c) produced by converting the isolated (S)-form compounds (8b).

The (R)-form enriched compounds (8b) prepared in EXAMPLE 12 were further purified by conducting at least one more enzymatic resolution and following guanidinolysis as described in EXAMPLES 10 and 12, and then the enantiomerically purified (100% e.e.) (R)-form compounds (8b) were obtained.

27

Step J: TBS-Protection—Synthesis of Isopropyl (3R, Z)-7-(3-(tert-butyldimethylsilyloxy)-5-oxo-cyclopent-1-enyl)-hept-5-enoate (8d)

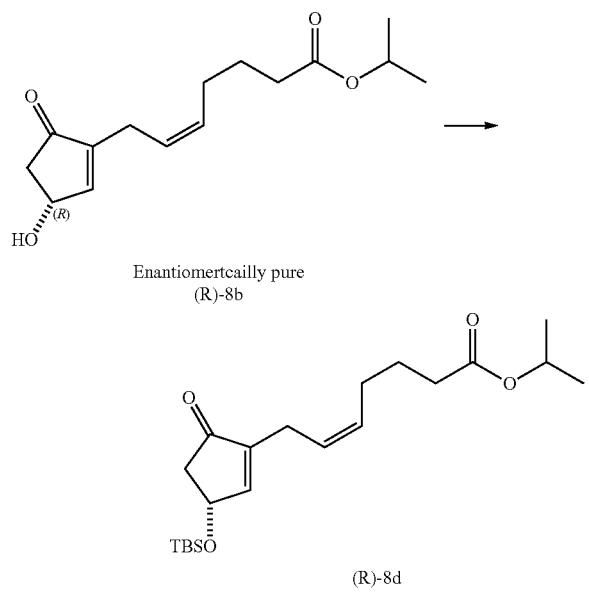

Enantiomertcailly pure
(R)-8b (R)-8d

Example 13

To a chilled solution of (R)-form compounds (8b) (about 3.4 Kg) prepared in EXAMPLE 12 and imidazole (about 1.6 Kg) in DMF (about 9 Kg) was added a solution of TBSCl (about 3 Kg) in DMF (about 12 Kg). The mixture was then stirred. The reaction was quenched with water (about 22 Kg) and extracted twice with MTBE (about 17 Kg each). The combined organic layer was washed with water (about 22 Kg) and then twice with saturated aqueous NaCl (about 22 Kg each). The organic layer was concentrated under reduced pressure and chromatographed to furnish (R)-form compounds (8d) (about 3.8 Kg, 98% GC pure). HPLC analysis showed that the (R)-form compounds (8d) contained 9.2% of the undesired trans-isomer.

Part II: Preparation of the Bottom Side Chains

Example 14

Synthesis of (3R,E)-3-(tert-butyldimethylsilyloxy)-1-(tributylstannyl)-4-(3-(trifluoromethyl)-phenoxy)-but-1-ene((R)-form 9a)

Step 1 Synthesis of Compounds (A3)

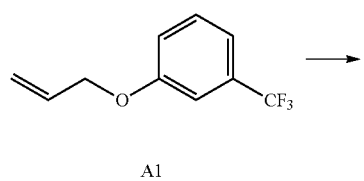

A1

28

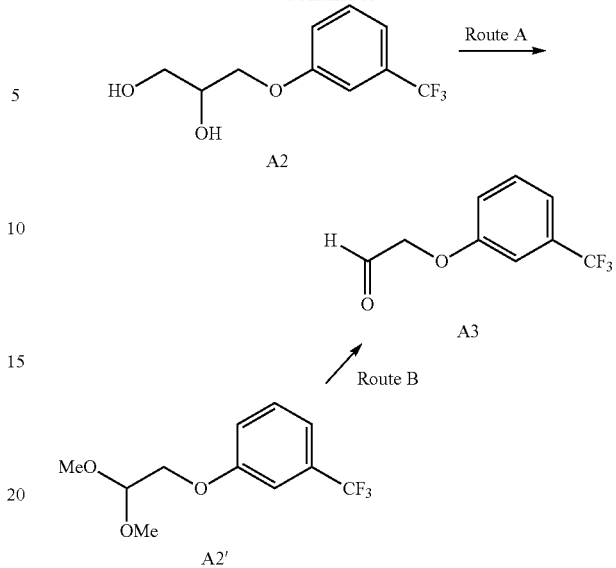

Route A:

To a solution of 3-(trifluoromethyl)phenol (about 200 g), allyl bromide (about 224 g) and THF (about 1.2 L) was added anhydrous $K_2CO_3$ (about 256 g). The mixture was then heated to 60-65° C. for 16 h, then filtered at 15-30° C. n-Heptane (about 400 mL) was added into the filtrate and the combined solution was washed with water (about 200 mL), saturated aq. KOH (about 300 mL) and saturated aq. NaCl (300 mL) and then concentrated at 45-50° C. under reduced pressure. 250 g of crude compound (A1) was obtained for the next step without purification.

A mixture of crude compound (A1) (250 g), potassium osmate (about 2 g) and $(DHQ)_2PHAL$ (about 5 g) in acetone (about 750 mL) was stirred and then cooled to 0-5° C. A solution of NMO (about 240 g) in water (about 500 mL) was added. $Na_2SO_3$ (about 200 g) was added to quench the reaction, and the mixture was then heated to 40-45° C. for 1 h, filtered and washed with acetone (about 50 mL). The combined filtrates were concentrated under reduced pressure. The concentrate was extracted twice with EtOAc (about 250 mL each), and the organic solution was washed with saturated aq. NaCl (about 200 mL), and then concentrated under reduced pressure. 281 g of crude compound (A2) was obtained.

To a stirred solution of $NaIO_4$ (about 72 g) in hot water (about 15 g) was added silica gel (about 360 g). The mixture was evaporated to give a powder, then DCM (about 800 mL) was added to the powder and cooled to 0-5° C. Crude compound (A2) (about 40 g) was added into the cold solution, the mixture was warmed and stirred. The reaction mixture was filtered, the filter cake was washed with DCM (about 50 mL), the combined filtrate were evaporated under reduced pressure giving 34 g of crude compound (A3).

Route B:

To a stirred solution of $K_2CO_3$ (about 5.7 Kg) and DMF (about 16 Kg) was added a mixture of trifluoromethylphenol (about 5.6 Kg) and 2-bromo-1,1-dimethoxyethane (about 7 Kg). The mixture was stirred at 140-150° C. Water (about 29 Kg) and MTBE (about 9 Kg) were added. After mixing the aqueous layer was extracted twice with MTBE (about 9 Kg each), and the organic solution was washed twice with water (about 9 Kg each) and then concentrated to furnish 99% GC pure compound (A2') (about 8.4 Kg, 96% yield). Alternatively, this reaction could be conducted in NMP solvent.

A mixture of compound (A2') (about 2.7 Kg), H$_2$SO$_4$ (2 M, about 15 Kg) and THF (about 13 Kg) under N$_2$ was heated under reflux. Toluene (about 11 Kg) was added into the reaction mixture and then was separated, the aqueous layer was extracted with toluene (about 11 Kg) and the combined organic solution was washed with saturated aqueous NaHCO$_3$ (about 2.5 L), twice with saturated aqueous NaCl (about 4 L each), dried over MgSO$_4$, filtered and concentrated to give 2.35 Kg (98% yield) of 92% GC pure compound (A3).

Step 2 Synthesis of the (R)-Form Compounds (A4)

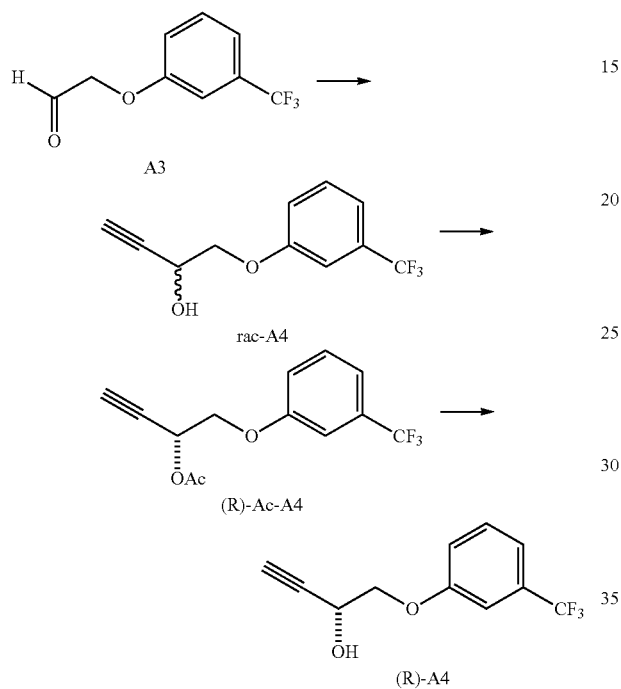

(Grignard Reaction)—To a cold solution of magnesium bromide acetylide (0.5 M, 24 L) under an atmosphere of N$_2$ was added a solution of crude compound (A3) (about 2.3 Kg in dry THF (about 25 L). The reaction mixture was stirred at 0-10° C. Saturated aq. NH$_4$Cl (about 10 L) and MTBE (about 8 Kg) were added to quench the reaction. The reaction mixture was separated and the separated aqueous layer was extracted with MTBE (8 Kg), the combined organic layer was washed twice with saturated aq. NaCl (about 4.5 L each) and concentrated under reduced pressure to provide 93% GC pure crude compounds (A4) in racemic form (about 2.05 Kg, 80% yield).

(Resolution)—A mixture of racemic compounds (A4) (about 5.6 Kg), Lipase PS "Amino" (about 2.8 Kg), vinyl acetate (about 7.6 Kg) and n-heptane (about 19 Kg) was stirred at 40° C. The reaction mixture was filtered through a layer of celite, and then concentrated to give a crude mixture of compounds (R)—Ac-A4 and (S)-form (A4).

(Mitsunobu reaction)—A mixture of compounds (R)—Ac-A4 and (S)-form (A4) prepared as described above, Ph$_3$P (about 9.8 Kg) and HCOOH (about 1.7 Kg) in THF (about 15 Kg) was cooled to 0-10° C. DEAD (about 6.5 Kg) in THF (about 10 Kg) was added at 0-10° C. The cooling was ceased and the reaction mixture was allowed to warm and stirred. The reaction mixture was concentrated under reduced pressure and then a mixture of EtOAc/n-heptane (1/3) was added and stirred for 15 minutes causing a white solid to precipitate. The mixture was filtered and the filter cake was washed three times with EtOAc/n-heptane (1/3), then concentrated and purified by column chromatography providing a mixture of (R)—Ac-A4 and the (R)-form (A4) formate.

(Guanidinolysis)—To a mixture of (R)—Ac-A4 and the (R)-form (A4) formate prepared above in MeOH (about 22 Kg) at −5 to 0° C., 0.5 M guanidine in MeOH (about 17 Kg) was added. AcOH (about 0.6 Kg) was added and the mixture was allowed to warm and then concentrated under reduced pressure to remove MeOH. EtOAc (about 15 Kg) was added to dissolve the residue and then the solution was washed with water (about 17 Kg), separated, and the aqueous layer was extracted with EtOAc (about 10 Kg). The combined organic layers were washed twice with saturated aq. NaCl (about 5.7 Kg each) and concentrated to give about 5 Kg of crude (R)-form compounds (A4) with about 90% e.e.

The (R)-form enriched compound (A4) prepared above was further purified by conducting at least one more Resolution directly followed by column chromatography to separate the desired (R)—Ac-A4 from the undesired (S)-form (A4). Then Guanidinolysis as described above and further column chromatography, was conducted to give the enantiomerically purified (>=99.0% e.e.) (R)-form compound (A4).

Step 3 Synthesis of the Compounds (9a)

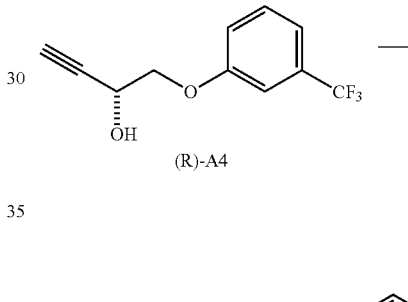

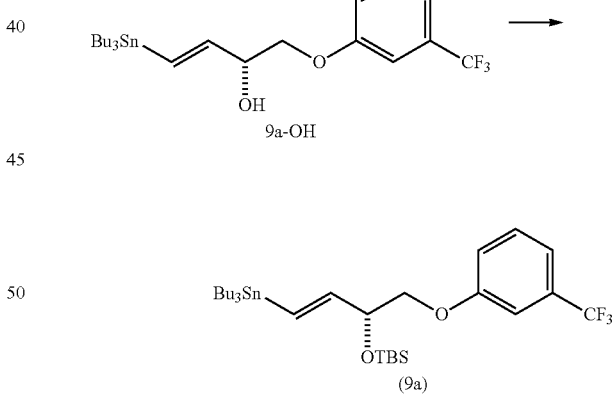

A mixture of (R)-form compounds (A4) (about 100 g), tributyltin hydride (Bu$_3$SnH) (about 140 g), azobis(isobutyronitrile) (AIBN) (about 7 g, catalytic) and toluene (about 300 mL) was heated at about 80° C. The reaction solution was evaporated and then purified by column chromatography to furnish about 117 g of compound (9a-OH).

To a solution of compound (9a-OH) (about 110 g), and imidazole (about 23 g) in dry DMF (about 0.3 L) at 0-10° C. under N$_2$, was added TBSCl (about 48 g) in DMF (about 0.5 L). The mixture was then stirred. The product mixture was diluted with n-heptane (about 0.7 L), washed with water (about 0.7 L) and the separated aqueous layer was extracted with n-heptane (about 0.36 L). The combined organic layer was washed twice with saturated aq. NaCl (about 0.56 L each) and optionally treated with triethylamine, concentrated to furnish 137 g (95% yield) of the (R)-form compound (9a).

Example 15

Synthesis of (3S,E)-3-(tert-butyldimethylsilyloxy)-5-phenyl-1-(tributylstannyl)-pent-1-ene)((S)-form 9b)

Step 1 Synthesis of the (S)-Form Compounds (B1)

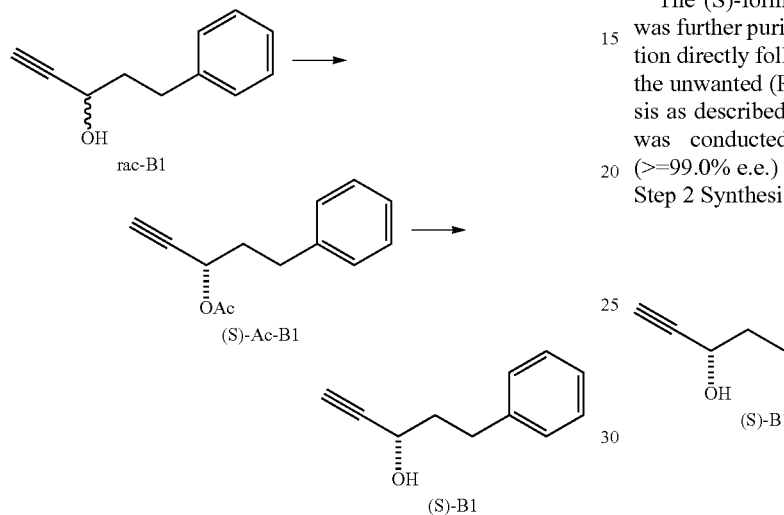

(Grignard Reaction)—To a cold solution of 0.5 M magnesium bromide acetylide in Et$_2$O (about 25 L) was added a solution of 3-phenyl-1-propanal (about 1.6 Kg) in THF (about 3 Kg). The reaction mixture was stirred. Saturated aq. NH$_4$Cl (about 7 L) was added into the reaction mixture causing a white precipitate to form. Water (about 7 L) was added to dissolve the precipitate. The solution was separated, the aqueous layer was extracted with MTBE (about 7 L), the combined organic solutions were dried over MgSO$_4$, filtered through silica gel with MTBE (about 10 L) and concentrated to furnish about 2 Kg (98% yield) of compounds (B1) in racemic form.

(Resolution)—A mixture of racemic compounds (B1) (about 4 Kg), Lipase PS "Amino" (about 2 Kg), vinyl acetate (about 5.0 Kg) and n-heptane (about 13 Kg) were stirred at about 40° C. The reaction mixture was filtered through a layer of celite and then concentrated to give about 4.4 Kg of a mixture of compounds (S)—Ac-B1 and (R)-form compound (B1).

(Mitsunobu reaction)—A mixture (about 4 Kg) of compounds (S)—Ac-B1 and (R)-form (B1) prepared as described above, Ph$_3$P (about 9 Kg) and HCOOH (about 1.6 Kg) in THF (about 15.7 Kg) was cooled to 0-10° C. DEAD (about 6 Kg) in THF (about 6.8 Kg) was added dropwise at 0-10° C. The cooling was ceased and the reaction mixture was allowed to warm and stirred. The reaction mixture was concentrated under reduced pressure and then a mixture of EtOAc/n-heptane (1/2) was added causing a white solid to precipitate. The mixture was filtered and the filter cake was washed three times with EtOAc/n-heptane (1/5), then concentrated and purified by column chromatography providing a mixture of (S)—Ac-B1 and the (S)-form (B1) formate.

(Guanidinolysis)—To a cold solution of compounds (S)—Ac-B1 and the (S)-form (B1) formate (about 5 Kg) in MeOH (about 15 Kg) was added 0.5 M guanidine in MeOH (about 19 Kg). The reaction mixture was stirred. AcOH (about 0.73 Kg) was then added and the mixture was evaporated under reduced pressure to remove the MeOH. The residue was dissolved in EtOAc (about 8.6 Kg) and washed with water (about 19 Kg), the layers were allowed to separate and the aqueous layer was extracted with EtOAc (about 8.6 Kg). The combined organic layer was washed twice with saturated aq. NaCl (about 12.6 Kg each) and concentrated to furnish about 4 Kg of crude (S)-form compound (B1) with about 84% e.e.

The (S)-form enriched compounds (B1) prepared above was further purified by conducting at least one more Resolution directly followed by column chromatography to remove the unwanted (R)-form compound (B1). Then Guanidinolysis as described above and further column chromatography was conducted to give the enantiomerically purified (>=99.0% e.e.) (S)-form compound (B1).

Step 2 Synthesis of the (S)-Form Compounds (9b)

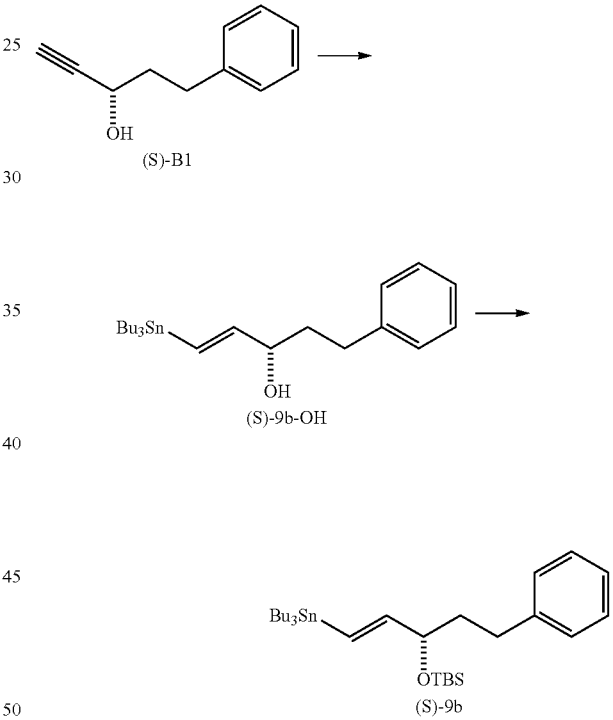

A mixture of (S)-form compound (B1) (about 147 g), Bu$_3$SnH (about 295 g), AIBN (about 16.6 g) and toluene (about 0.4 L) were stirred at 80-90° C. The reaction mixture was evaporated and then purified by column chromatography to give 193 g (45% yield) of compound (S)-9b-OH.

To the cold solution of compound (S)-9b-OH (about 190 g) and imidazole (about 58 g) in dry DMF (about 0.4 L) was added TBSCl (about 96 g) in DMF (about 0.6 L) under N$_2$. The mixture was then stirred. The product mixture was diluted with n-heptane (about 1 L), washed with water (about 1 L) and the separated aqueous layer was extracted with n-heptane (about 1 L). The combined organic layer was washed twice with saturated aq. NaCl (about 1 L each) and concentrated to furnish 245 g (95% yield) the (S)-form compounds (9b).

Part III: Coupling the Diverging Intermediate with the Bottom Side Chain to Give Prostaglandin Derivatives (A) Synthesis of Travoprost, Examples 16-18

Example 16

Michael Addition

Synthesis of Isopropyl (Z)-7-((1R,2R,3R)-2-((3R,E)-3-(tert-butyldimethylsilyloxy)-4-(3-(trifluoromethyl)phenoxy)-but-1-enyl)-3-(tert-butyldimethylsilyloxy)-5-oxo-cyclopentyl)-hept-5-enoate (10a)

To a cold solution of CuCN (about 16 g) in THF (300 mL) was added a solution of methyl lithium (MeLi) in diethyl ether (Et$_2$O) (1.6 M, 350 mL). After stirring for 10 minutes, the (R)-form compound (9a) (110 g) in THF (250 mL) was added and the solution was stirred. The reaction mixture was cooled to −80~−70° C. and a solution of the (R)-form compound (8d) (about 50 g) in THF (100 mL) was added. The reaction mixture was stirred. Saturated aqueous NH$_4$Cl (200 mL) was added, and then the reaction solution was warmed and filtered. The filter cake was washed with water (150 mL) and then with EtOAc (200 mL). The filtrate was separated and the aqueous layer was extracted twice with EtOAc (400 mL each). The combined organic layer was washed with saturated aqueous NaCl (400 mL) and then concentrated under reduced

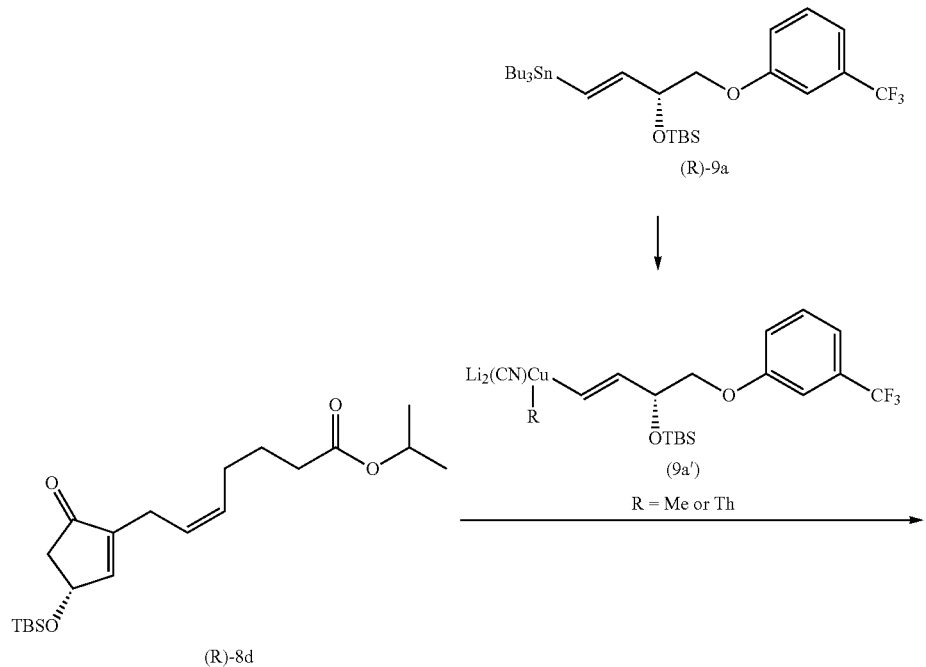

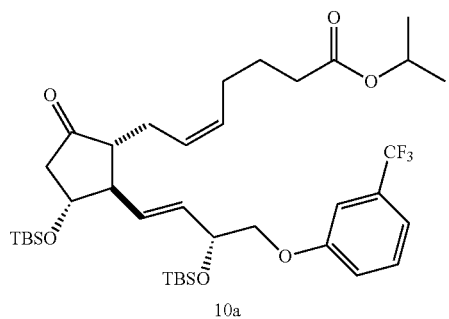

pressure to give 155 g of crude compound (10a). This material was used within a short period in EXAMPLE 17 as it is unstable.

The abovementioned Michael addition reaction also could be conducted by keeping the reaction at room temperature.

The abovementioned Michael addition reaction also could be conducted using a 2-thienylcyanocuprate prepared from (R)-form compound 9a.

Example 17

Ketone Reduction

Synthesis of Isopropyl (Z)-7-((1R,2R,3R,5S)-2-((3R,E)-3-(tert-butyldimethylsilyloxy)-4-(3-(trifluoromethyl)-phenoxy)-but-1-enyl)-3-(tert-butyldimethylsilyloxy)-5-hydroxy-cyclopentyl)-hept-5-enoate (11a)

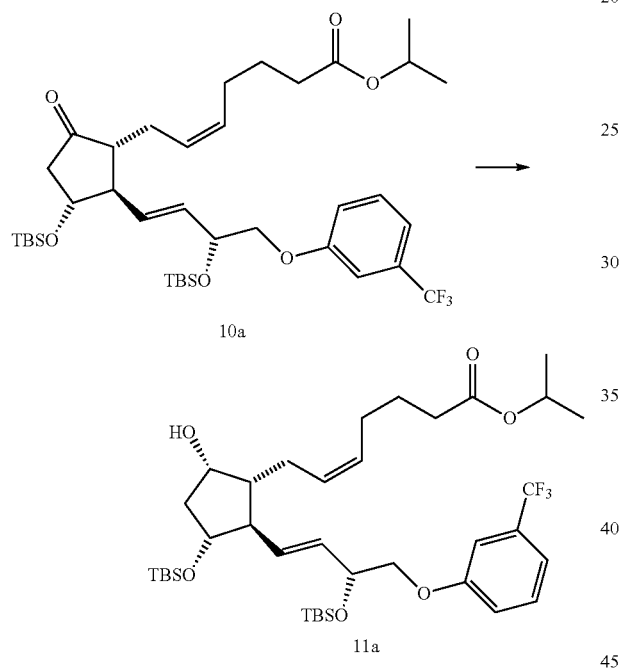

To a cold solution of crude compound (10a) (155 g) prepared in EXAMPLE 16 in THF (450 mL) was added a solution of L-Selectride in THF (1.06 M, 230 mL). 30% $H_2O_2$ (40 mL) was then added at −30° C., stirred for 1 h. Saturated aqueous NaCl (150 mL) was added into the reaction mixture, the layers were separated, the aqueous layer was extracted twice with MTBE or toluene (PhMe) (300 mL each) and then the combined organic layer was concentrated under reduced pressure. The crude product was purified by column chromatography to furnish 51.3 g of compound (11a) (92% HPLC purity, 50% yield). This was used directly in EXAMPLE 18.

The Ketone reduction was also conducted under the following conditions.

| Reagent | Solvent | Reaction temperature |
| --- | --- | --- |
| L-Selectride | PhMe/THF = 1.5:1 | −50 to −30° C. |
| NaBH$_4$ | THF | −5 to 0° C. |

Example 18

TBS-Deprotection

Synthesis of Isopropyl (Z)-7-((1R,2R,3R,5S)-3,5-dihydroxy-2-((3R,E)-3-hydroxy-4-(3-(trifluoromethyl)-phenoxy)-but-1-enyl)-cyclopentyl)-hept-5-enoate (Travoprost)

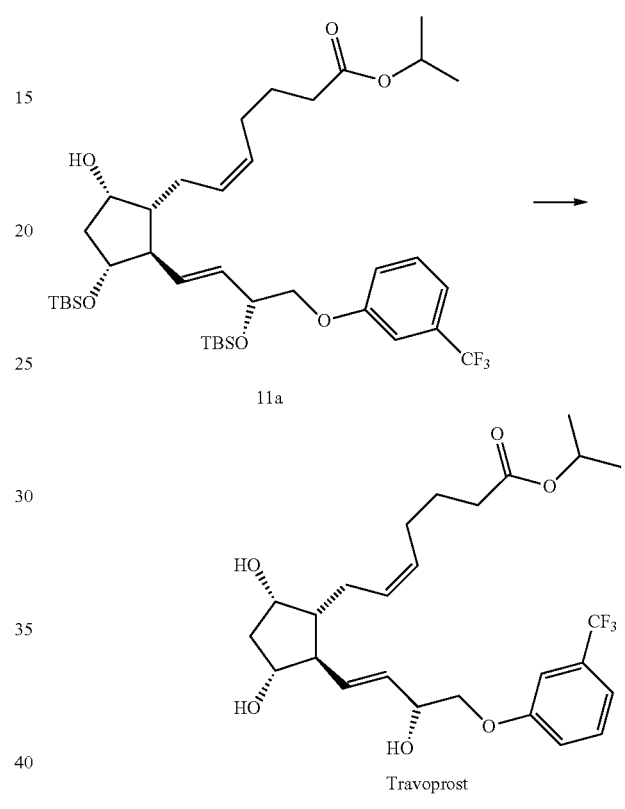

A mixture of crude compound (11a) (10 g), 2N HCl (37 mL) and isopropanol (IPA) (100 mL) was stirred. The reaction solution was neutralized with saturated aqueous NaHCO$_3$ and extracted twice with EtOAc (80 mL each), once with saturated aqueous NaCl (80 mL) and then the organic layer was concentrated under reduced pressure. The product was purified twice by column chromatography using mixtures of EtOAc and n-heptane to afford Travoprost (HPLC>99.0%).

Characterization of Travoprost:

$^1$H NMR (300 MHz, CDCl$_3$): δ 1.22 (d, J=6.3 Hz, 6H), 1.56 (septet, J=5.1 Hz, 1H), 1.66 (t, J=7.2 Hz, 2H), 1.81 (dd, J=2.85 Hz, 14.85 Hz, 1H), 2.26 (m, 7H), 2.40 (m, 1H), 2.53 (bs, 1H), 3.13 (bs, 2H), 3.99 (m, 3H), 4.19 (t, J=1.05 Hz, 1H), 4.55 (m, 1H), 5.00 (septet, J=6.3 Hz, 1H), 5.39 (m, 2H), 5.71 (m, 2H), 7.11 (dd, J=2.55 Hz, 8.1 Hz, 1H), 7.15 (s, 1H), 7.24 (d, J=7.8 Hz, 1H), 7.39 (t, J=7.95 Hz, 1H).

m/z (API-ES, Pos): 539 (MK$^+$, 8), 523 (MNa$^+$, 100), 501 (MH$^+$, 10), 321 (60).

The TBS-Deprotection was also conducted under the following conditions. The yields and HPLC purities of the resulting Travoprost are also listed. The crude travoprost could be further purified by repeated column chromatography.

| Reagent | Solvent | Reaction temperature | Yield; HPLC Purity |
|---------|---------|---------------------|--------------------|
| TBAF    | THF     | 40-45° C.           | 70%; 91.8%         |
| 4% HF   | IPA     | 40-45° C.           | 30%; 89%           |

(B) Synthesis of Bimatoprost, Examples 19-22

Example 19

Michael Addition

Synthesis of Isopropyl (Z)-7-((1R,2R,3R)-2-((3S,E)-3-(tert-butyldimethylsilyloxy)-5-phenyl-pent-1-enyl)-3-(tert-butyldimethylsilyloxy)-5-oxo-cyclopentyl)-hept-5-enoate (10b)

To a cold solution of CuCN (about 40 g) in THF (480 mL) was added a solution of MeLi in $Et_2O$ (1.6 M, 650 mL). After stirring for 5 minutes, the reaction mixture was warmed and (S)-form compound (9b) (about 260 g) in THF (770 mL) was added. The reaction mixture was cooled to between −80~−70° C. and (R)-form compound (8d) (about 130 g) in THF (about 130 mL) was added. The reaction mixture was stirred. Saturated aqueous $NH_4Cl$ (700 mL) was added to the cold product mixture at about −70° C., the solution was then warmed and filtered and the filter cake was washed with EtOAc (1.2 L). The filtrate was separated, the aqueous layer was extracted with EtOAc (250 mL), the combined organic layer was washed twice with saturated aqueous NaCl (500 mL each) and was then concentrated under reduced pressure to give 393 g of crude compound (10b). This material was unstable and was used directly in EXAMPLE 20.

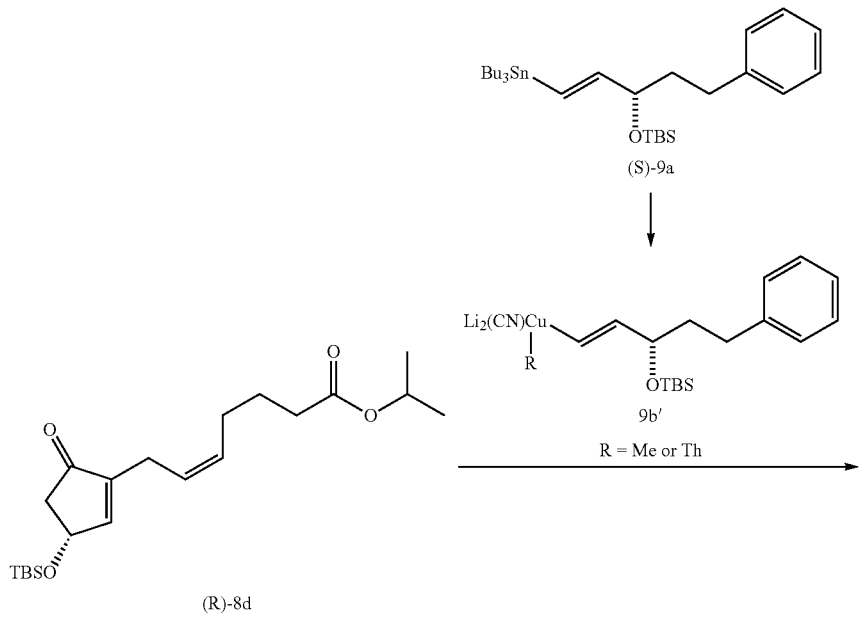

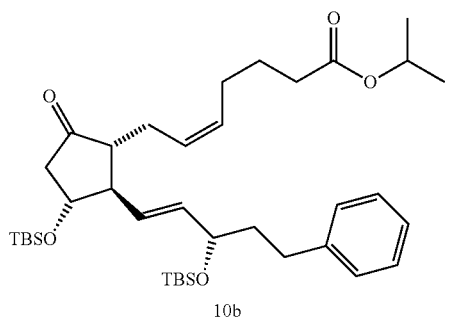

Alternatively, the Michael addition also could be conducted under the conditions described in EXAMPLE 16, such as using racemic starting materials, n-BuLi and ThCu(CN)Li.

Example 20

Ketone Reduction

Synthesis of Isopropyl (Z)-7-((1R,2R,3R,5S)-2-((3S,E)-3-(tert-butyldimethylsilyloxy)-5-phenyl-pent-1-enyl)-3-(tert-butyldimethylsilyloxy)-5-hydroxy-cyclopentyl)-hept-5-enoate (11b)

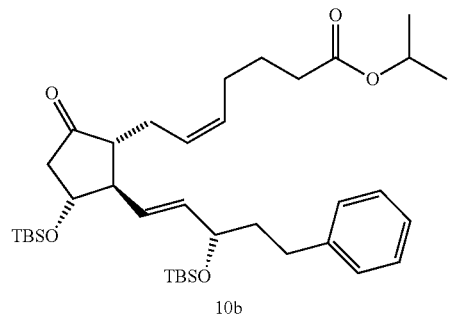

10b

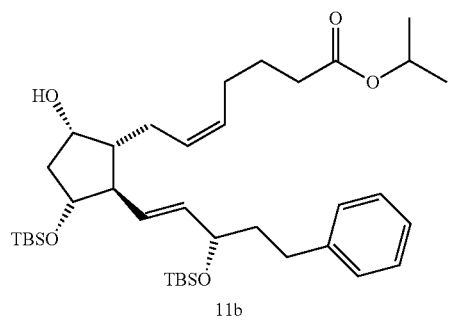

11b

To a cold solution of crude compound 10b (about 400 g) prepared in EXAMPLE 19 in THF (1.2 L) was added a solution of L-selectride in THF (1 M, 400 mL) with stirring. 30% $H_2O_2$ (150 mL) was added at −30° C., the mixture was warmed and then stirred for 0.5 h. Saturated aqueous NaCl (1400 mL) was added and the mixture was extracted twice with MTBE (1 L each), concentrated under reduced pressure. The crude product was purified by column chromatography to give about 120.5 g of compound (11b).

This Ketone Reduction was also conducted by using $NaBH_4$ in MeOH and keeping at −5 to 0° C.

Example 21

TBS-Deprotection

Synthesis of Isopropyl (Z)-7-((1R,2R,3R,5S)-3,5-dihydroxy-2-((3S,E)-3-hydroxy-5-phenyl-pent-1-enyl)-cyclopentyl)-hept-5-enoate (11c)

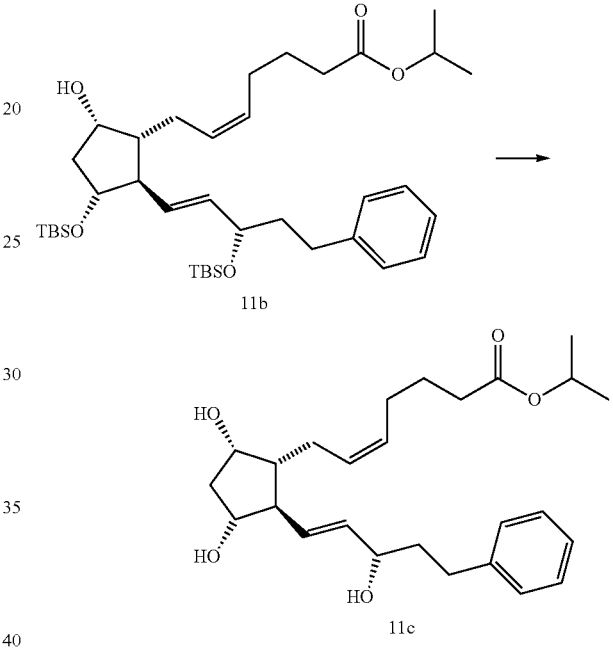

A solution of compound (11b) (60 g) prepared in EXAMPLE 20 and aqueous HF (2 N, 135 mL) in IPA (240 mL) was stirred. Saturated aqueous $NaHCO_3$ (120 mL) was added and the mixture was extracted with EtOAc (600 mL). The separated aqueous layer was extracted with EtOAc (300 mL) and the combined organic layer was washed with saturated aqueous NaCl (300 mL), dried with $Na_2SO_4$, filtered, and the filter cake was washed with EtOAc (200 mL). The filtrate was concentrated to furnish 43.5 g of crude compound (11c) (84.3% HPLC purity, 84% yield) which was directly used without purification in EXAMPLE 22.

This TBS-Deprotection was also conducted under the following conditions.

| Reagent | Solvent | Reaction temperature |
| --- | --- | --- |
| TBAF | THF | 50° C. |
| 2M HCl | IPA | 20-30° C. |
| 2M HCl | MeOH | 20-30° C. |
| 2M HCl | THF | 20-30° C. |

Example 22

Amination

Synthesis of (Z)-7-((1R,2R,3R,5S)-3,5-dihydroxy-2-((3S,E)-3-hydroxy-5-phenyl-pent-1-enyl)-cyclopentyl)-N-ethyl-hept-5-enamide (Bimatoprost)

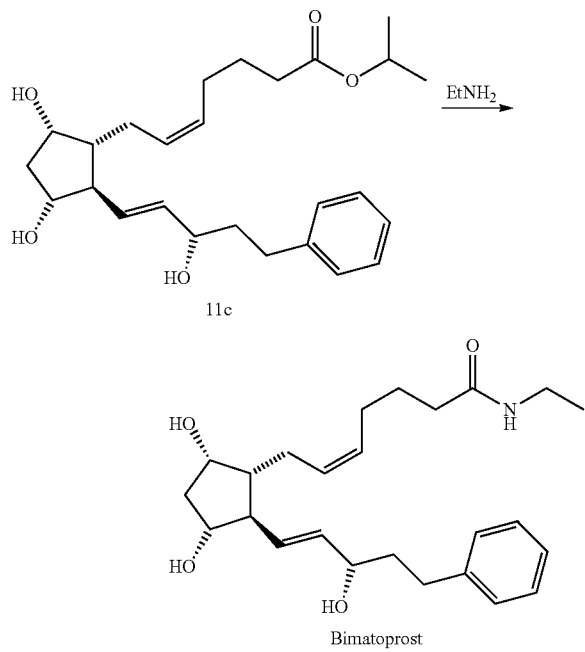

A solution of compound (11c) (about 40 g) prepared in EXAMPLE 21 in MeOH (44 mL) and 45% $EtNH_2$ in MeOH (800 mL) was heated to about 90° C. The reaction mixture was cooled to about 30° C. and concentrated under vacuum to remove MeOH to provide 45 g of crude product. This was purified by column chromatography to furnish 27 g (94.8% HPLC purity, 73% yield) of crude Bimatoprost. A solution of Bimatoprost (27 g) in MeOH (about 26 mL) and MTBE (about 800 mL) was heated until the solution became clear, and then was cooled down. The resulting crystals were filtered and the filter cake was washed twice with MTBE (150 mL each) and dried under reduced pressure to give 22 g (99.7% HPLC purity, 62% yield based on compound 11c) of Bimatoprost. This could be further purified to 99.9% HPLC purity Bimatoprost by recrystallization.

Characterization of Bimatoprost:

$^1$H NMR (300 MHz, $CD_3OD$): δ 1.09 (t, J=7.2 Hz, 3H), 1.50 (m, 1H), 1.62 (m, 3H), 1.83 (m, 2H), 2.11 (m, 8H), 2.68 (septet, J=7.5 Hz, 2H), 3.15 (q, J=7.2 Hz, 2H), 3.83 (m, 1H), 4.03 (t, J=6.45 Hz, 1H), 4.09 (m, 1H), 5.36 (m, 1H), 5.50 (m, 2H), 5.62 (d, J=6.3 Hz, 1H), 7.20 (m, 5H), 7.89 (br., 1H).

m/z (API-ES, Neg): 460 ([M+HCOO]$^-$, 100%).

The invention is not limited by the embodiments described above which are presented as examples only but can be modified in various ways within the scope of protection defined by the appended patent claims.

We claim:

1. A process for preparing a prostaglandin analogue of formula (11)

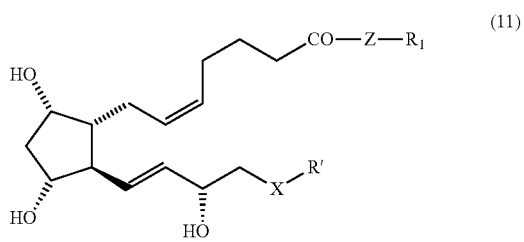

wherein
  $R_1$ represents H, $C_1$-$C_5$-alkyl, or benzyl;
  X represents $CH_2$, O, or S;
  Z represents O or NH; and
  R' represents $C_2$-$C_4$-alkyl; phenyl optionally substituted by halogen, $C_1$-$C_5$-alkyl, $C_1$-$C_4$-alkoxy, $CF_3$, $C_2$-$C_4$-polyhaloalkyl, or $C_1$-$C_3$-aliphatic acylamino; 5- or 6-membered heterocycle containing one or more hetero atoms selected from a group consisting of nitrogen, oxygen and sulfur; $C_3$-$C_7$-cycloalkyl; or $C_3$-$C_7$-cycloalkenyl;
the process comprise a step of converting a compound of formula (8'):

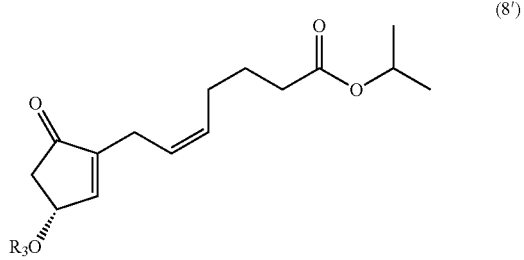

to the compound of formula (11), wherein $R_3$ represents hydrogen or a hydroxyl protecting group.

2. The process of claim 1 wherein the compound of formula (11) is travoprost.

3. The process of claim 1 wherein the compound of formula (11) is bimatoprost.

4. The process of claim 1 wherein the compound of formula (11) is bimatoprost, $R_3$ in the formula (8') represents a hydroxy-protecting group, and the step of converting comprises: a) reacting the compound of formula (8') with a compound of formula (9B):

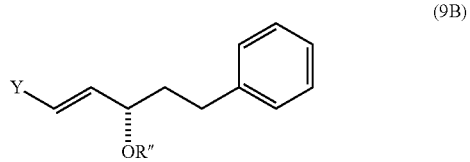

to give a compound of formula (10B):

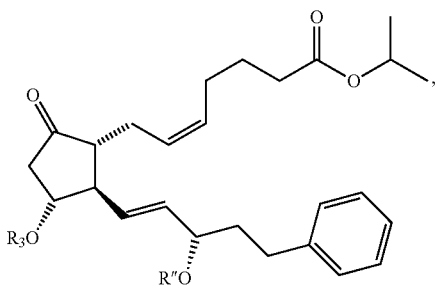
(10B)

and (b) converting the compound of formula (10B) to bimatoprost;

wherein Y represents a metal complex, R″ represents a hydroxy-protecting group.

5. The process of claim 4 wherein the step (b) comprising steps of:
(1) reducing the ketone group of compound of formula (10B);
(2) deprotecting the reduced form of the compound of formula (10B); and
(3) reacting the resultant compound of step (2) with ethylamine to give the bimatoprost.

6. The process of claim 5 wherein the step (3) is conducted in the presence of 40 to 80% v/v ethylamine in methanol.

7. The process of claim 4 wherein the step (b) comprising steps of:
(1) reducing the ketone group of compound of formula (10B);
(2) reacting the reduced compound of step (1) with ethylamine; and
(3) deprotecting the resultant compound of step (2) to give the bimatoprost.

8. The process of claim 7 wherein the step (2) is conducted in the presence of 40 to 80% v/v ethylamine in methanol.

* * * * *